United States Patent
Chen

[11] Patent Number: 6,051,578
[45] Date of Patent: Apr. 18, 2000

[54] PYRAZOLOPYRIMIDINES FOR TREATMENT OF CNS DISORDERS

[75] Inventor: Yuhpyng L. Chen, Waterford, Conn.

[73] Assignee: Pfizer Inc., New York, N.Y.

[21] Appl. No.: 09/150,688

[22] Filed: Sep. 10, 1998

Related U.S. Application Data

[63] Continuation of application No. 08/790,346, Jan. 27, 1997, abandoned.

[30] Foreign Application Priority Data

Feb. 12, 1996 [EP] European Pat. Off. ............. 96300931

[51] Int. Cl.$^7$ .................................................. A61K 31/505
[52] U.S. Cl. .............................................................. 514/258
[58] Field of Search ............................................. 514/258

[56] References Cited

U.S. PATENT DOCUMENTS

| | | |
|---|---|---|
| 2,965,643 | 12/1960 | Druey et al. . |
| 3,600,389 | 8/1971 | Druey et al. . |
| 4,213,977 | 7/1980 | Schane et al. . |
| 4,229,453 | 10/1980 | Roth et al. . |
| 4,904,666 | 2/1990 | Friebe et al. . |
| 5,063,245 | 11/1991 | Abreu et al. ............................. 514/404 |
| 5,646,152 | 7/1997 | Bright et al. ............................. 514/258 |
| 5,674,998 | 10/1997 | Boyer et al. ........................ 536/27.13 |

FOREIGN PATENT DOCUMENTS

| | | |
|---|---|---|
| 0005205 | 11/1979 | European Pat. Off. . |
| 0496617 | 7/1992 | European Pat. Off. . |
| 0691128 | 1/1996 | European Pat. Off. . |
| 3145287 | 5/1983 | Germany . |
| 93/11333 | 11/1993 | WIPO . |
| 93/10715 | 5/1994 | WIPO . |
| 9413643 | 6/1994 | WIPO . |
| 9413676 | 6/1994 | WIPO . |
| 9413677 | 6/1994 | WIPO . |
| WO 94/18215 | 8/1994 | WIPO . |
| 9510506 | 4/1995 | WIPO . |
| 9533750 | 12/1995 | WIPO . |

OTHER PUBLICATIONS

Lyons M.K. et al, Brain Res. (Netherlands) vol, 545, No. 1–2 1991, pp. 339–342.
Widmaier E.P. et al. Am. J. Physiol. vol. 255 No. 3—pp. 287–292, 1988.
Haines S. T. et al. Ann. Pharmacoter. vol. 28, No. 6, 1994, p. 781.
Klawans H. L. et al., Clinical Neuropharmacology, vol. 9, No. 2, 1986, pp. 202–205.
Owens, M.J. et al. "Physiology and Pharmacology of Corticotropin–releasing factor" *Pharm. Rev.*, vol. 43, 1991, pp. 425–473.
Robins, *Can. J. Chem.*, 55, 1251 (1977).
Senga et al. *J. Heterocyclic Chem.*, 19, 1565 (1982).
DeRoth, L., *Annals New York Acc. Sci.*, 1993, p. 285.
Strijbos P.J.L..M. et al Brain Res. (Netherlands) vol. 656, No. 2, 1994, pp. 405–408.
Search Report for EP 9630093, 1997.

*Primary Examiner*—William R. A. Jarvis
*Attorney, Agent, or Firm*—Peter C. Richardson; Paul H. Ginsburg; Seth Jacobs

[57] ABSTRACT

This invention relates to the use of pyrazolopyrimidines and pyrrolopyrimidine of, respectively, the general formula

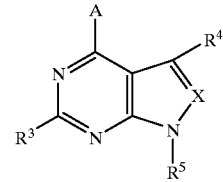

I wherein A, X, $R^3$, $R^4$ and $R^5$ are as defined below, and the pharmaceutically acceptable salts of such compounds, to treat, prevent or inhibit certain neuronal and other disorders.

28 Claims, No Drawings

PYRAZOLOPYRIMIDINES FOR TREATMENT OF CNS DISORDERS

This application is a continuation of Ser. No. 08/790,346, filed Jan. 27, 1997, now abandoned.

This invention relates to the use of pyrazolopyrimidines and pyrrolopyrimidines of the general formula

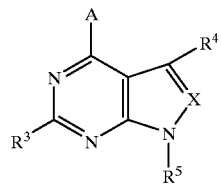

wherein A, X, $R^3$, $R^4$ and $R^5$ are as defined below, and the pharmaceutically acceptable salts of such compounds, to treat or prevent certain neuronal and other disorders.

The compounds of the formula I above exhibit corticotropin-releasing factor (CRF) receptor antagonist activity and are useful in the treatment and prevention of head trauma, spinal cord trauma, ischemic neuronal damage (e.g., cerebral ischemia such as cerebral hippocampal ischemia), excitotoxic neuronal damage, epilepsy, stroke, stress induced immune dysfunctions, phobias, muscular spasms, Parkinson's disease, Huntington's disease, urinary incontinence, senile dementia of the Alzheimer's type, multiinfarct dementia, amyotrophic lateral sclerosis, chemical dependencies and addictions (e.g., dependencies on alcohol, cocaine, heroin, benzodiazepines, or other drugs), and hypoglycemia.

The compounds of formula I are also useful for treatment of stress induced diseases in various livestock animal species caused by transportation (shipment) conditions such as a severe confining environment, exposure to a novel environment, confrontation with unfamiliar animals, noise, movement, hunger or thirst (e.g., bovine shipping fever, pasteurellosis, porcine stress syndrome or equine paroxysmal atrial fibrillation).

Certain substituted pyrrolopyrimidines have been referred to in the scientific literature. U.S. Pat. No. 4,229,453, which issued on Oct. 21, 1980, refers to 4-amino substituted pyrrolopyrimidines for treating CNS illnesses or inflammations. Robins, *Can. J. Chem.*, 55, 1251 (1977), refers to the antibiotic tubercidin having a 7-ribofuranosyl group attached to 4-aminopyrrolopyrimidine. German Patent Application 3145287, which was published on May 19, 1983, refers to three 7-bromophenyl-5,6-dimethylpyrrolopyrimidines as having analgesic, sedative, anti-convulsant and anti-inflammatory activity.

Certain substituted pyrazolopyrimidines have also been referred to in the literature. For instance, European Patent Application 496,617, which was published on Jul. 29, 1992, refers to adenosine kinase inhibitors, among which are 1-ribofuranosylpyrazolopyrimidines and 1-(substituted ribofuranosyl)pyrazolopyrimidines. U.S. Pat. No. 4,904,666, which issued on Feb. 27, 1990; refers to pyrazolopyrimidines having 1-tetrahydrofuranyl or 1-tetrahydropyranyl substituents. Senga et al, *J. Heterocyclic Chem.*, 19, 1565 (1982) refers to certain pyrazolopyrimidines having xanthine oxidase inhibitory activity. Other pyrazolopyrimidines are mentioned in U.S. Pat. Nos. 2,965,643 and 3,600,389, which issued, respectively, on Dec. 20, 1960 and Aug. 17, 1971.

Compounds of the formula I wherein X is nitrogen and the pharmaceutically acceptable acid addition salts of such compounds, as well as methods for preparing such compounds and salts, are referred to in World Patent Application PCT/US 93/11333, which designates the United States and was filed on Nov. 26, 1993 as a continuation-in-part of U.S. Ser. No. 992,229, which has since been abandoned. This World Patent Application also refers to the use of compounds of the formula I in the treatment of illnesses induced or facilitated by corticotropin releasing factor and in the treatment of inflammatory disorders such as arthritis, asthma and allergies, anxiety, depression, fatigue syndrome, headache, pain, cancer, irritable bowel syndrome, Crohn's disease, spastic colon, immune dysfunction, human immunodefiency virus (HIV) infections, neurodegenerative diseases such as Alzheimer's disease, gastrointestinal diseases, eating disorders such as anorexia nervosa, hemorrhagic stress, drug and alcohol withdrawal symptoms, drug addiction, stress-induced psychotic episodes and fertility problems.

Compounds of the formula I wherein X is $CR^6$ and the pharmaceutically acceptable acid addition of such compounds, as well as methods of preparing such compounds and salts, are referred to in World Patent Application PCT/US 93/10715, which designates the Unites States and was filed on May 5, 1994 as a continuation-in-part of U.S. Ser. No. 991,764, which has since been abandoned. This World Patent Application also refers to the use of compounds of the formula I wherein X is $CR^6$ in the treatment of illnesses induced or facilitated by corticotropin releasing factor and in the treatment of inflammatory disorders such as arthritis, asthma and allergies, anxiety, depression, fatigue syndrome, headache, pain, cancer, irritable bowel syndrome, Crohn's disease, spastic colon, immune dysfunction, human immunodeficiency virus (HIV) infections, neurodegenerative diseases such as Alzheimer's disease, gastrointestinal diseases, eating disorders such as anorexia nervosa, hemorrhagic stress, drug and alcohol withdrawal symptoms, drug addiction, stress-induced psychotic episodes and fertility problems.

World Patent Applications PCT/US 93/11333 and PCT/US 93/10715, as well as U.S. Ser. Nos. 992,229 and 991,764 referred to above, are incorporated herein by reference in their entireties.

SUMMARY OF THE INVENTION

This invention relates to a method of treating, preventing or inhibiting a disorder selected from head traumas, spinal cord trauma, ischemic neuronal damage (e.g., cerebral ischemia such as cerebral hippocampal ischemia), excitotoxic neuronal damage, epilepsy, stroke, stress induced immune dysfunctions, (e.g., porcine stress syndrome, obsessive-compulsive disorder, bovine shipping fever, equine paroxysmal fibrillation, phobias and dysfunctions induced by confinement in chickens, sheering stress in sheep or human-animal interaction related stress in dogs), phobias, muscular spasms, Parkinson's disease, Huntington's disease, urinary incontinence, senile dementia of the Alzheimer's type, multiinfarct dementia, amyotrophic lateral sclerosis, chemical dependencies and addictions (e.g., dependencies on alcohol, cocaine, heroin, benzodiazepines, or other drugs), and hypoglycemia in a mammal, including a human, comprising administering to such mammal an amount of a compound of the formula

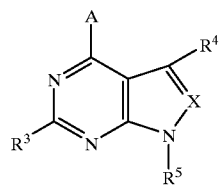

I wherein

X is nitrogen or —$CR^6$;

A is —$NR^1R^2$, —$CR^1R^2R^{11}$, —$C(=CR^2R^{12})R^1$, —$NHCR^1R^2R^{11}$, —$OCR^1R^2R^{11}$, —$SCR^1R^2R^{11}$, —$NHNR^1R^2$, —$CR^2R^{11}NHR^1$, —$CR^2R^{11}OR^1$, —$CR^2R^{11}SR^1$, or —$C(O)R^2$;

$R^1$ is hydrogen, or $C_1$–$C_6$ alkyl which may optionally be substituted with from one to two substituents independently selected from the group consisting of hydroxy, fluoro, chloro, bromo, iodo, $C_1$–$C_8$ alkoxy,

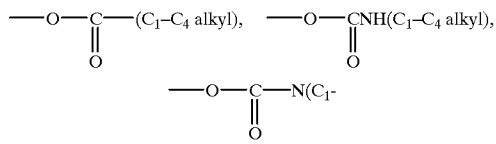

$C_4$ alkyl)($C_1$–$C_2$ alkyl), amino, —NH($C_1$–$C_4$ alkyl), —N($C_1$–$C_2$ alkyl)(C–$C_4$ alkyl), —S($C_1$–$C_6$ alkyl),

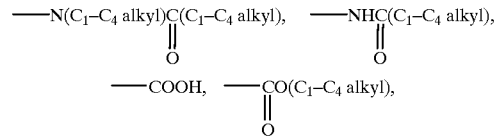

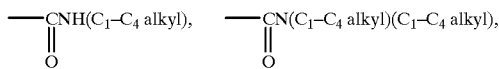

—SH, —CN, —$NO_2$, —SO($C_1$–$C_4$ alkyl), —$SO_2$($C_1$–$C_4$ alkyl), —$SO_2NH$($C_1$–$C_4$ alkyl), —$SO_2N$($C_1$–$C_4$ alkyl)(($C_1$–$C_2$ alkyl), and wherein each of the foregoing $C_1$–$C_6$ alkyl moieties in the definition of $R^1$ may contain one or two double or triple bonds;

$R^2$ is $C_1$–$C_{12}$ alkyl, aryl or —($C_1$–$C_{10}$ alkylene)aryl wherein said aryl is phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzisothiazolyl, thiazolyl, isoxazolyl, benzisoxazolyl, benzimidazolyl, triazolyl, pyrazolyl, pyrrolyl, indolyl, pyrrolopyridyl, oxazolyl, or benzoxazolyl; 3- to 8-membered cycloalkyl or —($C_1$–$C_6$ alkylene) cycloalkyl, wherein one or two of the carbon atoms of any of said cycloalkyl moieties may optionally be replaced, independently, by O, S or N-Z wherein Z is hydrogen, $C_1$–$C_4$ alkyl or $C_1$–$C_4$ alkanoyl, and wherein $R^2$ may optionally be substituted with from one to three substituents independently selected from chloro, fluoro and $C_1$–$C_4$ alkyl, or by one substituent selected from hydroxy, bromo, iodo, $C_1$–$C_6$ alkoxy,

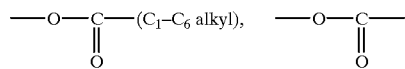

N($C_1$–$C_4$ alkyl)($C_1$–$C_2$ alkyl), —S($C_1$–$C_6$ alkyl), —$NH_2$, —NH($C_1$–$C_2$ alkyl), —N($C_1$–$C_2$ alkyl)($C_1$–$C_4$ alkyl),

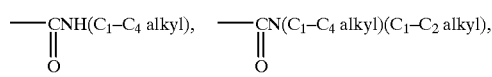

—SH, —CN, —$NO_2$, —SO($C_1$–$C_4$ alkyl), —$SO_2$($C_1$–$C_4$ alkyl), —$SO_2NH$($C_1$–$C_4$ alkyl), and —$SO_2N$($C_1$–$C_4$ alkyl)($C_1$–$C_2$ alkyl), and wherein each of the foregoing $C_1$–$C_{12}$ alkyl and $C_1$–$C_{10}$ alkylene moieties in the definition may optionally contain one to three double or triple bonds; or $R^1$ and $R^2$, taken together with the atom to which they are attached, may form a saturated 3- to 8-membered ring which, if it is a 5- to 8-membered ring, may optionally contain one or two double bonds, and wherein one or two of the carbon atoms of said 5- to 8- membered ring may optionally be replaced, independently, by O, S or N-Z wherein Z is hydrogen, $C_1$–$C_4$ alkyl, $C_1$–$C_4$ alkanoyl or benzyl;

$R^3$ is hydrogen, $C_1$–$C_6$ alkyl, fluoro, chloro, bromo, iodo, hydroxy, amino, —O($C_1$–$C_6$ alkyl), —NH($C_1$–$C_6$ alkyl), —N($C_1$–$C_4$ alkyl)($C_1$–$C_2$ alkyl), —SH, —S($C_1$–$C_4$ alkyl), —SO($C_1$–$C_4$ alkyl), or —$SO_2$($C_1$–$C_4$ alkyl), wherein each of the foregoing $C_1$–$C_4$ alkyl and $C_1$–$C_6$ alkyl moieties in the definition of $R^3$ may contain one double or triple bond and may optionally be substituted with from 1 to 3 substituents independently selected from the group consisting of hydroxy, $C_1$–$C_3$ alkoxy, fluoro, chloro and $C_1$–$C_3$ thioalkyl;

$R^4$ is hydrogen, $C_1$–$C_6$ alkyl, fluoro, chloro, bromo, iodo, $C_1$–$C_6$ alkoxy, formyl, —NH($C_1$–$C_6$ alkyl), —N($C_1$–$C_6$ alkyl)($C_1$–$C_2$ alkyl), —$SO_n$($C_1$–$C_6$ alkyl), wherein n is 0, 1 or 2, cyano, hydroxy, carboxy, or amido, wherein each of the foregoing $C_1$–$C_6$ alkyl moieties in the definition of $R^3$ may optionally be substituted with one substituent selected from hydroxy, trifluoromethyl, amino, carboxy, amido,

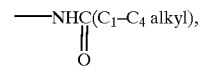

—NH($C_1$–$C_4$ alkyl). —N($C_1$–$C_4$ alkyl)($C_1$–$C_2$ alkyl),

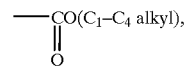

$C_1$–$C_3$ alkoxy, $C_1$–$C_3$ thioalkyl, fluoro, bromo, chloro, iodo, cyano and nitro;

$R^5$ is phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzoisothiazolyl, thiazolyl, isoxazolyl, benzisoxazolyl, benzimidazolyl, triazolyl, pyrazolyl, pyrrolyl, indolyl, pyrrolopyridyl, benzoxazolyl, oxazolyl, pyrrolidinyl, thiazolindinyl, morpholinyl, piperidinyl, piperazinyl, tetrazolyl, or a 3- or 8-membered cycloalkyl or 9- or 12-membered bicycloalkyl ring, wherein one or two of the carbon atoms in said ring may optionally be replaced, independently, by O, S or N-Z wherein Z is hydrogen, $C_1$–$C_4$ alkyl, $C_1$–$C_4$ alkanoyl, phenyl or benzyl, and wherein each of the above $R^5$ groups may optionally be substituted with one or more substituents, preferably with two or three substituents, independently selected from fluoro, chloro, bromo, formyl, $C_1$–$C_6$ alkyl, $C_1$–$C_6$ alkoxy and trifluoromethyl, or with one substituent selected from hydroxy, iodo, cyano, nitro, amino, —NH($C_1$–$C_4$ alkyl), —N($C_1$–$C_4$ alkyl)($C_1$–$C_2$ alkyl), —COO($C_1$–$C_4$ alkyl), —CO($C_1$–$C_4$ alkyl), —$SO_2$NH($C_1$–$C_4$ alkyl), —$SO_2$N ($C_1$–$C_4$ alkyl)($C_1$–$C_2$ alkyl), —$SO_2NH_2$, —$NHSO_2$($C_1$–$C_4$ alkyl), —S($C_1$–$C_6$ alkyl), —$SO_2$($C_1$–$C_6$ alkyl), and wherein each of the foregoing $C_1$–$C_4$ alkyl and $C_1$–$C_6$ alkyl moieties in the definition of $R^5$ may optionally be substituted with from one to two substituents independently selected from fluoro, chloro, hydroxy, $C_1$–$C_4$ alkoxy, amino, methylamino, dimethylamino and acetyl, and wherein each of the foregoing $C_1$–$C_4$ alkyl and $C_1$–$C_6$ alkyl moieties in the definition of $R^5$ may optionally contain one double or triple bond; with the proviso that $R^5$ is not unsubstituted phenyl;

$R^6$ is hydrogen, $C_1$–$C_6$ alkyl, fluoro, chloro, bromo, iodo, $C_1$–$C_6$ alkoxy, formyl, amino, —NH($C_1$–$C_6$ alkyl), N($C_1$–$C_6$ alkyl)($C_1$–$C_2$ alkyl), —$SO_n$($C_1$–$C_6$ alkyl), wherein n is 0, 1 or 2, cyano, carboxy, or amido, and wherein each of the foregoing ($C_1$–$C_6$)alkyl moieties in the definition of $R^6$ may be optionally substituted with one substituent selected from hydroxy, trifluoromethyl, amino, carboxy, amido,

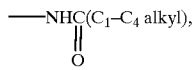

—NH($C_1$–$C_4$ alkyl), —N($C_1$–$C_4$ alkyl)($C_1$–$C_2$ alkyl),

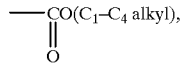

$C_1$–$C_3$ alkoxy, $C_1$–$C_3$ thioalkyl, fluoro, bromo, chloro, iodo, cyano and nitro;

$R^{11}$ is hydrogen, hydroxy, fluoro, chloro, —COO($C_1$–$C_2$ alkyl), cyano, or —CO($C_1$–$C_2$ alkyl); and $R^{12}$ is hydrogen or $C_1$–$C_4$ alkyl;

with the proviso that: (1) when X is —$CR^6$, A is not straight chain alkyl; (2) when X is $CR^6$ and $R^5$ is unsubstituted cycloalkyl and $R^3$ and $R^4$ are both hydrogen and $R^6$ is hydrogen or methyl, then A is not $NHR^2$ wherein $R^2$ is benzyl or thienylmethyl, and (3) when X is —$CR^6$ and $R^5$ is p-bromophenyl and $R^3$, $R^4$ and $R^6$ are methyl, then A is not methylamino or hydroxyethylamino;

and when X is nitrogen, with the further proviso that:

(a) A is not straight chain $C_1$–$C_{12}$ alkyl;

(b) $R^5$ is not a sugar group;

(c) when $R^3$ and $R^4$ are hydrogen and $R^5$ is chlorophenyl, then A is not —NH—CH($CH_3$)—($CH_2$)$_3$—($C_2H_5$)$_2$;

(d) when $R^3$ and $R^4$ are hydrogen and A is —$NR^1R^2$ wherein $R^1$ is $C_3$–$C_7$ cycloalkyl, and $R^2$ is $C_2$–$C_6$ alkenyl, phenyl-($C_1$–$C_6$ alkylene) or hetero-($C_1$–$C_6$ alkylene) wherein the hetero radical is furyl, thienyl or pyridinyl, and wherein said phenyl may be substituted with one or more substituents independently selected from fluoro, chloro, bromo and iodo, then $R^5$ is not tetrahydrofuranyl or tetrahydropyranyl;

(e) when $R^3$ is methoxy, methylthio, or methylsulfonyl, $R^4$ is hydrogen, and $R^5$ is tetrahydrofuranyl or tetrahydropyranyl, then A is not —NH($C_1$–$C_2$alkyl), morpholinyl, hydrazino, or —$NHC_2H_4C_6H_5$, the phenyl of which may be substituted by one methyl or two methoxy groups;

(f) when $R^3$ is hydrogen, $C_1$–$C_6$ alkyl, chloro, bromo, —SH, or —S—($C_1$–$C_4$ alkyl), $R^4$ is hydrogen and $R^5$ is $C_3$–$C_8$ cycloalkyl, then A is not hydrazino, —NH ($C_1$–$C_2$ alkyl) or —N($C_1$–$C_6$ alkyl) ($C_1$–$C_{12}$ alkyl);

(g) when $R^3$ and $R^4$ are hydrogen and A is —NH($CH_2$)$_m$COOH wherein m is 1–12, then $R^5$ is not phenyl substituted by one fluoro, chloro, bromo or iodo group;

(h) when $R^3$ is hydrogen, hydroxy, methylthio, chloro or —NHbenzyl, $R^4$ is hydrogen, and $R^5$ is chlorophenyl or bromophenyl, then A is not —NH($C_1$–$C_{12}$ alkyl), —NHallyl, or —N($C_1$–$C_6$ alkyl) ($C_1$–$C_{12}$ alkyl), wherein said $C_1$–$C_{12}$ alkyl may be substituted by —$NC_2H_5$, or —NH benzyl which may be substituted by one or two bromo, chloro, fluoro, —$NC_2H_5$ phenyl or morpholinopropyl groups;

(i) when $R^3$ and $R^4$ are hydrogen and $R^5$ is nitrophenyl, then A is not —$NHR^2$ wherein $R^2$ is phenyl, benzyl or $C_1$–$C_{12}$ alkyl which may be substituted by one or two hydroxy groups;

(j) when $R^3$ is chloro or —O($C_1$–$C_6$ alkyl), $R^4$ is hydrogen, and A is —$NR^1R^2$ wherein $R^1$ and $R^2$ are independently hydrogen or $C_1$–$C_6$ alkyl, then $R^5$ is not chlorophenyl; and (k) when $R^3$ is hydrogen, A is benzyl or phenethyl, and $R^4$ is fluoro, chloro, bromo or iodo, then $R^5$ is not 5'-deoxy-ribofuranosyl or 5'-amino-5'-deoxy-ribofuranosyl;

or a pharmaceutically acceptable salt thereof, that is effecting in treating or preventing such disorder. The foregoing method is hereinafter also referred to as "Method A".

The term "halo", as used herein, unless otherwise indicated, includes chloro, fluoro, bromo and iodo.

The term "alkyl", as used herein, unless otherwise indicated, includes saturated monovalent hydrocarbon radicals having straight, branched or cyclic moieties or combinations thereof.

The term "one or more substituents," as used herein, includes from one to the maximum number of substituents possible based on the number of available bonding sites.

The compounds of formula I have chiral centers and therefore exist in different enantiomeric forms. This invention relates to all optical isomers and all stereoisomers of compounds of the formula I, and mixtures thereof.

Formula I above includes compounds identical to those depicted but for the fact that one or more hydrogen, nitrogen or carbon atoms are replaced by radioactive isotopes thereof. Such radiolabelled compounds are useful as research and diagnostic tools in metabolism pharmokinetic studies and in binding assays.

"Ischemic neuronal damage" includes, for example, neuronal damage resulting from CNS surgery, open heart surgery or procedures during which the function of the cardiovascular system is compromised.

"Stress induced immune dysfunctions" include deficiencies in the immune system in both man and animals that are stress induced. For example, such dysfunctions include (but are not limited to) porcine stress syndrome, obsessive-compulsive disorder, bovine shipping fever, equine paroxysmal fibrillation, phobias and dysfunctions induced by confinement stress in livestock animals (e.g., chicken, cows, pigs, sheep, etc.), sheering stress in sheep or human-animal interaction related stress in dogs. (See DeRoth, L., "Stress and Disease in Domestic Animals", pp. 285 et al. in *Annals New York Acc. Sci.,* 1993; Liptrap, R. M., "Stress and Reproduction in Domestic Animals", pp. 275–282 in *Annals New York Acc. Sci.,* 1993; and Dallaire, A., "Stress and Behavior in Domestic Animals", p. 269–273 in *Annals New York Acc. Sci.,* 1993).

This invention also relates to a method of treating or preventing a disorder selected from head trauma, spinal cord trauma, ischemic neuronal damage (e.g., cerebral ischemia such as cerebral hippocampal ischemia), excitotoxic neuronal damage, epilepsy, stroke, stress induced immune dysfunctions, phobias, muscular spasms, Parkinson's disease, Huntington's disease, urinary incontinence, senile dementia of the Alzheimer's type, multiinfarct dementia, amyotrophic lateral sclerosis, chemical dependencies and additions (e.g., dependencies on alcohol, cocaine, heroin, benzodiazephines, or other drugs), and hypoglycemia in a mammal, including a human, comprising administering to such mammal a CRF receptor antagonizing amount of a compound of the formula I, as depicted and defined above, or a pharmaceutically acceptable salt thereof. The foregoing method is hereinafter also referred to as "Method B".

Preferred embodiments of this invention include Methods A and B, as described above, wherein the compound of formula I or the pharmaceutically acceptable salt of such compound that is employed is a compound wherein X is nitrogen and: (a) $R^1$ is $C_1$–$C_4$ alkyl, —$(C_2$–$C_4$ alkylene)O $(C_1$–$C_4$ alkyl), or $C_2$–$C_4$ hydroxyalkyl; (b) $R^2$ is $C_1$–$C_5$ alkyl, benzyl, phenylethyl, or benzyl substituted with one or two substituents independently selected from chloro, fluoro, methyl, ehtyl, methoxy, ethoxy and t-butyl, or by one trifluoromethyl group; (2-thienyl)methyl: (2-thienyl)ethyl; (2-furanyl)methyl; 2-(4-chlorothienyl)methyl; (2-benzofuranyl)methyl; (2-benzothienyl)methyl; (2-thiazolyl)methyl; or (2-benzothiazolyl)methyl; (c) $R^3$ is hydrogen, methyl, ethyl, methoxy, fluoro or chloro; (d) $R^4$ is hydrogen, methyl, ethyl, or n-propyl; and (e) $R^5$ is phenyl substituted with two or three substituents.

Other preferred embodiments of this invention include Methods A and B, as described above, wherein the compound of formula I or the pharmaceutically acceptable salt of such compound that is employed is a compound wherein X is $CR^6$ and: (a) $R^1$ is $C_1$–$C_4$ alkyl, —$(C_2$–$C_4$ alkylene)O $(C_1$–$C_4$ alkyl), or $C_2$–$C_4$ hydroxyalkyl; (b) $R^2$ is $C_1$–$C_5$ alkyl, benzyl, phenylethyl, or benzyl substituted with one or two substituents independently selected from chloro, fluoro, methyl, ethyl, methoxy, ethoxy and t-butyl, or by one trifluoromethyl group; (2-thienyl)methyl; (2-thienyl)ethyl; (2-furanyl)methyl; 2-(4-chlorothienyl)methyl; (2-benzofuranyl)methyl; (2-benzothienyl)methyl; (2-thiazolyl)methyl; or (2-benzothiazolyl)methyl; (c) $R^3$ is hydrogen, methyl, ethyl, methoxy, fluoro or chloro; (d) $R^4$ is hydrogen, methyl, ethyl, or n-propyl; (e) $R^5$ is phenyl substituted with two or three substituents; and (f) $R^6$ is hydrogen, methyl, ethyl or chloro; with the proviso that $R^2$ and $R^6$ are not both hydrogen.

Other preferred embodiments of this invention include Methods A and B, as described above, wherein the compound of formula I or the pharmaceutically acceptable salt of such compound that is employed is a compound wherein X is $CR^6$ and: (a) A is —$NR_1R^2$, —$NHCHR^1R^2$, or —$OCHR^1R^2$, wherein $R^1$ is $C_1$–$C_6$ alkyl which may optionally be substituted with one of hydroxy, fluoro and $C_1$–$C_2$ alkoxy, and may optionally contain one double or triple bond; (b) $R^2$ is benzyl or $C_1$–$C_6$ alkyl which may optionally contain one double or triple bond, wherein said $C_1$–$C_6$ alkyl or the phenyl moiety of said benzyl may optionally be substituted with one fluoro, $C_1$–$C_6$ alkyl, or $C_1$–$C_6$ alkoxy; (c) $R^3$ is methyl, ethyl, fluoro, chloro or methoxy; (d) $R^4$ and $R^6$ are independently selected from hydrogen, methyl and ethyl; and (e) $R^5$ is phenyl substituted with two or three substituents, said substituents being independently selected from fluoro, chloro, bromo, iodo, $C_1$–$C_4$ alkoxy, trifluoromethyl, $C_1$–$C_6$ alkyl which may optionally be substituted with one hydroxy group, $C_1$–$C_4$ alkoxy and fluoro and which may optionally contain one double or triple bond, —$(C_1$–$C_4$ alkylene)O$(C_1$–$C_2$ alkyl), $C_1$–$C_3$ hydroxyalkyl, hydroxy, formyl, —COO$(C_1$–$C_2$ alkyl), or —C(O)$(C_1$–$C_4$ alkyl).

Other preferred embodiments of this invention include Methods A and B, as described above, wherein the compound of formula I or the pharmaceutically acceptable salt of such compound that is employed is a compound wherein X is nitrogen and: (a) A is —$NR_1R^2$, —$NHCHR^1R^2$, or —$OCHR^1R^2$, wherein $R^1$ is $C_1$–$C_6$ alkyl which may optionally be substituted with one of hydroxy, fluoro and $C_1$–$C_2$ alkoxy, and may optionally contain one double or triple bond; (b) $R^2$ is benzyl or $C_1$–$C_6$ alkyl which may optionally contain one double or triple bond, wherein said $C_1$–$C_6$ alkyl or the phenyl moiety of said benzyl may optionally be substituted with one fluoro, $C_1$–$C_6$ alkyl, or $C_1$–$C_6$ alkoxy; (c) $R^3$ is methyl, ethyl, fluoro, chloro or methoxy; (d) $R^4$ and $R^6$ are independently selected from hydrogen, methyl and ethyl; and (e) $R^5$ is phenyl substituted with two or three substituents, said substituents being independently selected from fluoro, chloro, bromo, iodo, $C_1$–$C_4$ alkoxy, trifluoromethyl, $C_1$–$C_6$ alkyl which may optionally be substituted with one hydroxy group, $C_1$–$C_4$ alkoxy and fluoro and which may optionally contain one double or triple bond, —$(C_1$–$C_4$ alkylene)O$(C_1$–$C_2$ alkyl), $C_1$–$C_3$ hydroxyalkyl, hydroxy, formyl, —COO$(C_1$–$C_2$ alkyl), or —C(O)$(C_1$–$C_4$ alkyl).

Other embodiments of this invention include Methods A and B, as described above, wherein the compound of formula I or the pharmaceutically acceptable salt of such compound that is employed is a compound wherein X is nitrogen and: (a) A is —$NR_1R^2$, —$NHCHR^1R^2$, or —$OCHR^1R^2$, wherein $R^1$ is $C_1$–$C_6$ alkyl, which may optionally be substituted by one hydroxy, fluoro or $C_1$–$C_2$ alkoxy group, and which may optionally contain one double or triple bond, and $R^2$ is benzyl or $C_1$–$C_6$ alkyl which may optionally contain one double or triple bond, and wherein said $C_1$–$C_6$ alkyl or the phenyl moiety of said benzyl may optionally be substituted with fluoro, $C_1$–$C_6$ alkyl, or $C_1$–$C_6$ alkoxy; or (b) A is —$CR^1R^2R^{11}$ wherein $R^1$ is $C_1$–$C_6$ alkyl which may optionally be substituted with one $C_1$–$C_6$ alkoxy or hydroxy group, $R^2$ is benzyl or $C_1$–$C_6$ alkyl wherein said $C_1$–$C_6$ alkyl or the phenyl moiety of said benzyl may optionally be substituted by one $C_1$–$C_6$ alkyl, $C_1$–$C_6$ alkoxy, fluoro, chloro or bromo group, and $R^{11}$ is hydrogen or fluoro.

Other specific embodiments of this invention include Methods A and B, as described above, wherein the compound of formula I or the pharmaceutically acceptable salt of such compound that is employed is a compound wherein X is nitrogen and $R^2$ is —$(C_1$–$C_4$ alkylene)aryl, wherein said aryl is phenyl, thienyl, benzofuranyl, furanyl, benzothienyl, thiazolyl, pyridyl or benzothiazolyl.

Other specific embodiments of this invention include Methods A and B, as described above, wherein the compound of formula I or the pharmaceutically acceptable salt of such compound that is employed is a compound wherein X is nitrogen and $R^2$ is a benzyl group that is optionally substituted on the phenyl moiety with one ethyl, t-butyl, methoxy, trifluoromethyl, nitro, fluoro chloro, or methyl group.

Other specific embodiments of this invention include Methods A and B, as described above, wherein the compound of formula I or the pharmaceutically acceptable salt of such compound that is employed is a compound wherein X is nitrogen and $R^2$ is attached through a methylene or ethylene bridge to quinolyl, pyrrolyl, pyrrolidinyl, pyridyl, tetrahydropyranyl, cyclopropyl, piperidinyl, or benzylpiperidinyl.

Other specific embodiments of this invention include Methods A and B, as described above, wherein the compound of formula I or the pharmaceutically acceptable salt of such compound that is employed is a compound wherein X is nitrogen or $CR^6$ and $R^1$ and $R^2$ are, independently, $C_1$–$C_6$ alkyl which may optionally be substituted with one substituent selected from hydroxy, methoxy, ethoxy, chloro, fluoro, —OC(O)CH$_3$, —OC(O)NHCH$_3$, and —C(O)NH$_2$.

Other specific embodiments of this invention include Methods A and B, as described above, wherein the compound of formula I or the pharmaceutically acceptable salt of such compound that is employed is a compound wherein X is nitrogen or $CR^6$ and $R^2$ is $C_1$–$C_6$ alkyl which may optionally be substituted with one substituent selected from methoxy and ethoxy.

Other specific embodiments of this invention include Methods A and B, as described above, wherein the compound of formula I or the pharmaceutically acceptable salt of such compound that is employed is a compound wherein X is nitrogen and A is —NR$^1$R$^2$ or —CHR$^1$R$^2$ in which R$^1$ and R$^2$, together with the N or CH to which they are attached, form a 5- or 6-membered ring in which one of the ring carbon atoms may optionally be replaced by an oxygen or sulfur atom, e.g., pyrrolidinyl, pyrrolyl, pyrazolyl, imidazolyl, oxazolyl, thiazolyl, isoxazolyl, thiadiazolyl, oxadiazolyl, pyridyl, pyrazinyl or pyrimidyl.

Other specific embodiments of this invention include Methods A and B, as described above, wherein the compound of formula I or the pharmaceutically acceptable salt of such compound that is employed is a compound wherein X is nitrogen or $CR^6$ and A is —NHCHR$^1$R$^2$ or —OCHR$^1$R$^2$ in which —CHR$^1$R$^2$ is a 5- or 6-membered ring in which one of the ring carbon atoms may optionally be replaced by an oxygen or sulfur atom, e.g., tetrahydrofuranyl, tetrahydrothiafuranyl and cyclopentanyl.

Other specific embodiments of this invention include Methods A and B, as described above, wherein the compound of formula I or the pharmaceutically acceptable salt of such compound that is employed is a compound selected from the following:

3-{(4-methyl-benzyl)-[3,6-dimethyl-1-(2,4,6-trimethylphenyl)-1H-pyrazolo[3,4-d]pyrimidin-4yl]-amino}-propan-1-ol;

diethyl-[6-methyl-3-methylsulfanyl-1-(2,4,6-trichlorophenyl)-1H-pyrazolo[3,4-d]pyrimidin-4yl]-amine;

2-{butyl-[6-methyl-3-methylsulfanyl-1-(2,4,6-trichlorophenyl)-1H-pyrazolo[3,4-d]pyrimidin-4yl]-amino}-ethanol;

dibutyl-[6-methyl-3-methylsulfanyl-1-(2,4,6-trichlorophenyl)-1H-pyrazolo[3,4-d]pyrimidin-4yl}-amine;

butyl-ethyl-[6-methyl-3-methylsulfanyl-1-(2,4,6-trichlorophenyl)-1H-pyrazolo[3,4-d]pyrimidin-4yl]-amine;

butyl-ethyl-[6-methyl-3-methylsulfonyl-1-(2,4,6-trichlorophenyl)-1H-pyrazolo[3,4-d]pyrimidin-4yl]-amine;

butyl-cyclopropylmethyl-[6-methyl-3-methylsulfanyl-1-(2,4,6-trichlorophenyl)-1H-pyrazolo[3,4-d]pyrimidin-4yl]-amine;

di-1-propyl-[6-methyl-3-methylsulfanyl-1-(2,4,6-trichlorophenyl)-1H-pyrazolo[3,4-d]pyrimidin-4yl]-amine;

diallyl-[6-methyl-3-methylsulfanyl-1-(2,4,6-trichlorophenyl)-1H-pyrazolo[3,4-d]pyrimidin-4yl]-amine;

butyl-ethyl-[6-chloro-3-methylsulfanyl-1-(2,4,6-trichlorophenyl)-1H-pyrazolo[3,4-d]pyrimidin-4yl]-amine;

butyl-ethyl-[6-methoxy-3-methylsulfanyl-1-(2,4,6-trichlorophenyl)-1H-pyrazolo[3,4-d]pyrimidin-4yl]-amine;

propyl-ethyl-[3,6-dimethyl-1-(2,4,6-trimethylphenyl)-1H-pyrazolo[3,4-d]pyrimidin-4-yl]-amine;

4-(1-ethyl-propyl)-6-methyl-3-methylsulfanyl-1-(2,4,6-trimethylphenyl)-1H-pyrazolo[3,4-d]pyrimidine;

2-[3,6-dimethyl-1-(2,4,6-trimethylphenyl)-1H-pyrazolo[3,4-d]pyrimidin-4-ylamine]-butan-1ol;

[3,6-dimethyl-1-(2,4,6-trimethylphenyl)-1H-pyrazolo-[3,4-d]pyrimidin-4-yl]-(1-methylpropyl)amine;

4-(1-methoxymethylpropoxy)-3,6-dimethyl-1-(2,4,6-trimethylphenyl)-1H-pyrazolo[3,4-d]pyrimidine;

n-butyl-ethyl-[2,5-dimethyl-7-(2,4,6-trimethylphenyl)-7H-pyrrolo[2,3-d]pyrimidin-4-yl]amine;

di-n-propyl-[2,5-dimethyl-7-(2,4,6-trimethylphenyl)-7H-pyrrolo[2,3-d]pyrimidin-4-yl]amine;

ethyl-n-propyl-[2,5-dimethyl-7-(2,4,6-trimethylphenyl)-7H-pyrrolo[2,3-d]pyrimidin-4-yl]amine;

diethyl-2,5-dimethyl-7-(2,4,6-trimethylphenyl)-7H-pyrrolo[2,3-d]pyrimidin-4-yl]amine;

n-butyl-ethyl-[2,5,6-trimethyl-7-(2,4,6-trimethylphenyl)-7H-pyrrolo[2,3-d]pyrimidin-4-yl]amine;

2{N-n-butyl-N-[2,5-dimethyl-7-(2,4,6-trimethylphenyl)-7H-pyrrolo[2,3-d]pyrimidin-4-yl]amino}-ethanol;

4-(1-ethyl-propyl)-2,5,6-trimethyl-7-(2,4,6-trimethylphenyl)-7H-pyrrolo[2,3-d]pyrimidine;

n-butyl-ethyl-[2,5-dimethyl-7-(2,4-dimethylphenyl)-7H-pyrrolo[2,3-d]pyrimidin-4-yl]amine;

2,5-dimethyl-7-(2,4,6-trimethylphenyl)-7H-pyrrolo[2,3-d]pyrimidyl-4-yl]-(1-ethylpropyl)amine;

2-[7-(4-bromo-2,6-dimethylphenyl)-2,5-dimethyl-7H-pyrrolo[2,3-d]pyrimidin-4-ylamino]-butan-1-ol;

2-(S)-[7-(4-bromo-2,6-dimethylphenyl)-2,5-dimethyl-7H-pyrrolo[2,3-d]pyrimidin-4-ylamino]-butan-1-ol;

4-(1-ethyl-propoxy)-2,5,6-trimethyl-7-(2,4,6-trimethylphenyl)-7H-pyrrolo[2,3-d]pyrimidine;

4-(1-methoxymethyl-propoxy)-2,5,6-trimethyl-7-(2,4,6-trimethylphenyl)-7H-pyrrolo[2,3-d]pyrimidine;

4-(1-ethyl-butyl)-2,5,6-trimethyl-7-(2,4,6-trimethylphenyl)-7H-pyrrolo[2,3-d]pyrimidine;

[7-(4-bromo-2,6-dimethyl-phenyl)-2,5-dimethyl-7H-pyrrolo[2,3-d]pyrimidin-4yl]-(1-methoxymethyl-propyl)-amine;

2-[7-(2-bromo-4,6-dimethyl-phenyl)-2,5-dimethyl-7H-pyrrolo[2,3-d]pyrimidin-4ylamino]-butan-1-ol;

2-[7-(4-ethyl-2,6-dimethyl-phenyl)-2,5-dimethyl-7H-pyrrolo[2,3-d]pyrimidin-4ylamino]-butan-1-ol;

2-[7-(2-ethyl-4,6-dimethylphenyl)-2,5-dimethyl-7H-pyrrolo[2,3-d]pyrimidin-4ylamino]-butan-1-ol; and 2-[7-(2-fluoromethyl-4,6-dimethylphenyl)-2,5-dimethyl-7H-pyrrolo[2,3-d]pyrimidin-4ylamino]-butan-1-ol.

Whenever reference is made to alkyl, this includes both straight and branched chain alkyl.

Whenever reference is made herein to 3-to 8-membered cycloalkyl or 9- to 12-membered bicycloalkyl containing one to three of O, S or N-Z, it is understood that the oxygen and sulfur ring atoms are not adjacent to each other. The three membered cycloalkyl has just one O, S or N-Z. An example of a six-membered cycloalkyl having O and N is morpholinyl.

Whenever $R^2$ or $R^5$ is a heterocyclic group, the attachment of the group is through a carbon atom.

Whenever reference is made herein to $C_1$–$C_4$ alkyl or $C_1$–$C_6$ alkyl which "may contain one or two double or triple bonds" in the definitions of $R^1$, $R^2$ and $R^3$, it is understood that at least two carbons are present in the alkyl for one double or triple bond, and at least four carbons for two double and triple bonds.

Whenever an alkoxy group, e.g., in the definitions of $R^1$ and $R^2$, may have a double or triple bond, it is understood that such double or triple bond is not directly attached to the oxygen.

Formula I above is intended to include all stereoisomers (e.g., all geometric and optical isomers) as well as all racemates of all individual compounds within the depicted genus.

DETAILED DESCRIPTION OF THE INVENTION

Compounds of the formula I wherein X is nitrogen and the pharmaceutically acceptable acid addition of such compounds, as well as methods for preparing such compounds and salts, are referred to in World Patent Application PCT/US 93/11333, which designates the United States and was filed on Nov. 26, 1993 as a continuation-in-part of U.S. Ser. No. 992,229, which was filed on Dec. 17, 1992 and is now abandoned. The foregoing international and U.S. patent applications are incorporated herein by reference in their entireties.

Compounds of the formula I wherein X is $CR^6$ and the pharmaceutically acceptable acid addition of such compounds, as well as methods of preparing such compounds and salts, are referred to in World Patent Application PCT/US 93/10715, which designates the United States and was filed on May 5, 1994 as a continuation-in-part of U.S. Ser. No. 991,764, which was filed on Dec. 14, 1993 and is now abandoned. The foregoing international and U.S. patent applications are incorporated herein by reference in their entireties.

For use in carrying out the methods of this invention, compounds of the formula I and their pharmaceutically acceptable salts may be administered orally, topically or parenterally. They may be administered alone or in combination with pharmaceutically acceptable carriers, in either single or multiple, e.g. up to three, doses. Suitable pharmaceutical carriers include inert solid diluents or fillers, sterile aqueous solution and various organic solvents. The pharmaceutical compositions formed by combining the novel compounds of formula I and the pharmaceutically acceptable carriers are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. Oral compositions may also be administered in the form of a gel. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions of the novel compound of formula I in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

Additionally, it is possible to administer the compounds employed in the method of the present invention topically when treating inflammatory conditions of the skin and this may be done by way of creams, jellies, gels, pastes and ointments in accordance with standard pharmaceutical practice.

The compounds of formula I and the pharmaceutically acceptable salts thereof will generally be administered from one to three times per day (i.e., from one to three doses per day), with each dose containing from about 0.1 to about 100 mg/kg body weight, although variations will necessarily occur depending upon the weight and condition of the subject being treated, the nature and severity of the disorder for which the subject is being treated and the particular route of administration chosen. However, a dosage level that is in the range of about 1.0 mg to about 50 mg per kg of body weight per individual does will most desirably be employed. Variations may nevertheless occur depending upon the species of mammal being treated and the individual subject's response to said medicament, as well as on the type of pharmaceutical formulation chosen and the time period and interval at which such administration is carried out.

The methods for testing the compounds for formula I for their CRF antagonist activity are according to the procedures of *Endocrinology*, 116, 1653–1659 (1985) and *Peptides*, 10, 179–188 (1988), which determine the binding affinity of a test compound for a CRF receptor. The binding affinities for the compounds of formula I, expressed as $IC_{50}$ values, generally range from about 0.2 nanomolar to about 10 micromolar.

What is claimed is:

1. A method of treating, preventing or inhibiting a disorder selected from head trauma, spinal cord trauma, muscular spasms, urinary incontinence, multiinfarct dementia, and hypoglycemia in a mammal, comprising administering to said mammal in need thereof an amount of a compound of the formula

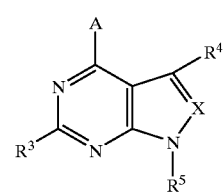

I wherein

X is nitrogen or —CR$^6$;

A is —NR$^1$R$^2$, —CR$^1$R$^2$R$^{11}$, —C(=CR$^2$R$^{12}$)R$^1$, —NHCR$^1$R$^2$R$^{11}$, —OCR$^1$R$^2$R$^{11}$, —SCR$^1$R$^2$R$^{11}$, —NHNR$^1$R$^2$, —CR$^2$R$^{11}$NHR$^1$, —CR$^2$R$^{11}$OR$^1$, —CR$^2$R$^{11}$SR$^1$, or —C(O)R$^2$;

R$^1$ is hydrogen, or C$_1$–C$_6$ alkyl which may optionally be substituted with from one to two substituents independently selected from the group consisting of hydroxy, fluoro, chloro, bromo, iodo, C$_1$–C$_8$ alkoxy, —O—(C$_1$–C$_6$ alkyl), —O—NH(C$_1$–C$_4$ alkyl), —O—N(C$_1$–C$_4$ alkyl)(C$_1$–C$_2$ alkyl), amino, —NH(C$_1$–C$_4$ alkyl), —N(C$_1$–C$_2$ alkyl)(C$_1$–C$_4$ alkyl), —S(C$_1$–C$_6$ alkyl), —N(C$_1$–C$_4$ alkyl)(C$_1$–C$_4$ alkyl), —NH(C$_1$–C$_4$ alkyl), —COOH, —O(C$_1$–C$_4$ alkyl), —NH(C$_1$–C$_4$ alkyl), —N(C$_1$–C$_4$ alkyl)(C$_1$–C$_2$ alkyl), —SH, —CN, —NO$_2$, —SO(C$_1$–C$_4$ alkyl), —SO$_2$(C$_1$–C$_4$ alkyl), —SO$_2$NH(C$_1$–C$_4$ alkyl), —SO$_2$(C$_1$–C$_4$ alkyl)(C$_1$–C$_2$ alkyl), and wherein each of the foregoing C$_1$–C$_6$ alkyl moieties in the definition of R$^1$ may contain one or two double or triple bonds;

R$^2$ is C$_1$–C$_{12}$ alkyl, aryl or —(C$_1$–C$_{10}$ alkylene)aryl wherein said aryl is phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzisothiazolyl, thiazolyl, isoxazolyl, benzisoxazolyl, benzimidazolyl, triazolyl, pyrazolyl, pyrrolyl, indolyl, pyrrolopyridyl, oxazolyl, or benzoxazolyl; 3- to 8-membered cycloalkyl or —(C$_1$–C$_6$ alkylene) cycloalkyl, wherein one or two of the carbon atoms of any of said cycloalkyl moieties may optionally be replaced, independently, by O, S or N-Z wherein Z is hydrogen, C$_1$–C$_4$ alkyl or C$_1$–C$_4$ alkanoyl, and wherein R$^2$ may optionally be substituted with from one to three substituents independently selected from chloro, fluoro and C$_1$–C$_4$ alkyl, or by one substituent selected from hydroxy, bromo, iodo, C$_1$–C$_6$ alkoxy, —O—(C$_1$–C$_6$ alkyl), —O—N(C$_1$–C$_4$ alkyl)(C$_1$–C$_2$ alkyl), —S(C$_1$–C$_6$ alkyl), —NH$_2$, —NH(C$_1$–C$_2$ alkyl), —N(C$_1$–C$_2$ alkyl) (C$_1$–C$_4$ alkyl), —N(C$_1$–C$_4$ alkyl)-(C$_1$–C$_4$ alkyl), —NH(C$_1$–C$_4$ alkyl), —COOH, —O(C$_1$–C$_4$ alkyl), —NH(C$_1$–C$_4$ alkyl), —N(C$_1$–C$_4$ alkyl)(C$_1$–C$_2$ alkyl), —SH, —CN, —NO$_2$, —SO(C$_1$–C$_4$ alkyl), —SO$_2$(C$_1$–C$_4$ alkyl), —SO$_2$NH(C$_1$–C$_4$ alkyl), and —SO$_2$N(C$_1$–C$_4$ alkyl)(C$_1$–C$_2$ alkyl), and wherein each of the foregoing C$_1$–C$_{12}$ alkyl and C$_1$–C$_{10}$ alkylene moieties in the definition may optionally contain one to three double or triple bonds; or R$^1$ and R$^2$, taken together with the atom to which they are attached, may form a saturated 3- to 8-membered ring which, if it is a 5- to 8-membered ring, may optionally contain one to two double bonds, and wherein one or two of the carbon atoms of said 5- to 8- membered ring may optionally be replaced, independently, by O, S or N-Z wherein Z is hydrogen, C$_1$–C$_4$ alkyl, C$_1$–C$_4$ alkanoyl or benzyl;

R$^3$ is hydrogen, C$_1$–C$_6$ alkyl, fluoro, chloro, bromo, iodo, hydroxy, amino, —O(C$_1$–C$_6$ alkyl), —NH(C$_1$–C$_6$ alkyl), —N(C$_1$–C$_4$ alkyl)(C$_1$–C$_2$ alkyl), —SH, —S(C$_1$–C$_4$ alkyl), —SO(C$_1$–C$_4$ alkyl), or —SO$_2$(C$_1$–C$_4$ alkyl), wherein each of the foregoing C$_1$–C$_4$ alkyl and C$_1$–C$_6$ alkyl moieties in the definition of R$^3$ may contain one double or triple bond and may optionally be substituted with from 1 to 3 substituents independently selected from the group consisting of hydroxy, C$_1$–C$_3$ alkoxy, fluoro, chloro and C$_1$–C$_3$ thioalkyl;

R$^4$ is hydrogen, C$_1$–C$_6$ alkyl, fluoro, chloro, bromo, iodo, C$_1$–C$_6$ alkoxy, formyl, —NH(C$_1$–C$_6$ alkyl), —N(C$_1$–C$_6$ alkyl)(C$_1$–C$_2$ alkyl), —SO$_n$(C$_1$–C$_6$ alkyl), wherein n is 0, 1 or 2, cyano, hydroxy, carboxy, or amido, wherein each of the foregoing C$_1$–C$_6$ alkyl moieties in the definition of R$^4$ may optionally be substituted with one substituent selected from hydroxy, trifluoromethyl, amino, carboxy, amido, —NH(C$_1$–C$_4$ alkyl), —NH(C$_1$–C$_4$ alkyl), —N(C$_1$–C$_4$ alkyl)(C$_1$–C$_2$ alkyl), —O(C$_1$–C$_4$ alkyl), C$_1$–C$_3$ alkoxy, C$_1$–C$_3$ thioalkyl, fluoro, bromo, chloro, iodo, cyano and nitro;

R$^5$ is phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzoisothiazolyl, thiazolyl, isoxazolyl, benzisoxazolyl, benzimidazolyl, triazolyl, pyrazolyl, pyrrolyl, indolyl, pyrrolopyridyl, benzoxazolyl, oxazolyl, pyrrolidinyl, thiazolindinyl, morpholinyl, piperidinyl, piperazinyl, tetrazolyl, or a 3- or 8-membered cycloalkyl or 9- or 12-membered bicycloalkyl ring, wherein one or two of the carbon atoms in said ring may optionally be replaced, independently, by O, S or N-Z wherein Z is hydrogen, C$_1$–C$_4$ alkyl, C$_1$–C$_4$ alkanoyl, phenyl or benzyl, and wherein each of the above R$^5$ groups may optionally be substituted with one or more substituents, preferably with two or three substituents, independently selected from fluoro, chloro, bromo, formyl, C$_1$–C$_6$ alkyl, C$_1$–C$_6$ alkoxy and trifluoromethyl, or with one substituent selected from hydroxy, iodo, cyano, nitro, amino, —NH(C$_1$–C$_4$ alkyl), —N(C$_1$–C$_4$ alkyl)(C$_1$–C$_2$ alkyl), —COO(C$_1$–C$_4$ alkyl), —CO(C$_1$–C$_4$ alkyl), —SO$_2$NH(C$_1$–C$_4$ alkyl), —SO$_2$N(C$_1$–C$_4$ alkyl)(C$_1$–C$_2$ alkyl), —SO$_2$NH$_2$, —NHSO$_2$(C$_1$–C$_4$ alkyl), —S(C$_1$–C$_6$ alkyl), —SO$_2$ (C$_1$–C$_6$ alkyl), and wherein each of the foregoing C$_1$–C$_4$ alkyl and C$_1$–C$_6$ alkyl moieties in the definition of R$^5$ may optionally be substituted with from one to two substituents independently selected from fluoro, chloro, hydroxy, C$_1$–C$_4$ alkoxy, amino, methylamino, dimethylamino and acetyl, and wherein each of the foregoing C$_1$–C$_4$ alkyl and C$_1$–C$_6$ alkyl moieties in the definition of R$^5$ may optionally contain one double or triple bond; with the proviso that R$^5$ is not unsubstituted phenyl;

R$^6$ is hydrogen, C$_1$–C$_6$ alkyl, fluoro, chloro, bromo, iodo, C$_1$–C$_6$ alkoxy, formyl, amino, —NH(C$_1$–C$_6$ alkyl), N(C$_1$–C$_6$ alkyl)(C$_1$–C$_2$ alkyl), —SO$_n$(C$_1$–C$_6$ alkyl), wherein n is 0, 1 or 2, cyano, carboxy, or amido, and wherein each of the foregoing (C$_1$–C$_6$)alkyl moieties in the definition of R$^6$ may be optionally substituted with one substituent selected from hydroxy, trifluoromethyl, amino, carboxy, amido, —NH(C$_1$–C$_4$ alkyl), —NH(C$_1$–C$_4$ alkyl), —N(C$_1$–C$_4$ alkyl)(C$_1$–C$_2$ alkyl), —O(C$_1$–C$_4$ alkyl), C$_1$–C$_3$ alkoxy, C$_1$–C$_3$ thioalkyl, fluoro, bromo, chloro, iodo, cyano and nitro;

R$^{11}$ is hydrogen, hydroxy, fluoro, chloro, —COO(C$_1$–C$_2$ alkyl), cyano, or —CO(C$_1$–C$_2$ alkyl); and R$^{12}$ is hydrogen or C$_1$–C$_4$ alkyl;

with the proviso that:

(1) when X is —CR$^6$, A is not straight chain alkyl;

(2) when X is CR$^6$ and R$^5$ is unsubstituted cycloalkyl and R$^3$ and R$^4$ are both hydrogen and R$^6$ is hydrogen or methyl, then A is not NHR$^2$ wherein R$^2$ is benzyl or thienylmethyl, and (3) when X is —CR$^6$ and R$^5$ is p-bromophenyl and R$^3$, R$^4$ and R$^6$ are methyl, then A is not methylamino or hydroxyethylamino;

and when X is nitrogen, with the further proviso that:

(a) A is not straight chain $C_1$–$C_{12}$ alkyl;

(b) $R^5$ is not a sugar group;

(c) when $R^3$ and $R^4$ are hydrogen and $R^5$ is chlorophenyl, then A is not —NH—CH($CH_3$)—$(CH_2)_3$—$(C_2H_5)_2$;

(d) when $R^3$ and $R^4$ are hydrogen and A is —$NR^1R^2$ wherein $R^1$ is $C_3$–$C_7$ cycloalkyl, and $R^2$ is $C_2$–$C_6$ alkenyl, phenyl-($C_1$–$C_6$ alkylene) or hetero-($C_1$–$C_6$ alkylene) wherein the hetero radical is furyl, thienyl or pyridinyl, and wherein said phenyl may be substituted by fluoro, chloro, bromo and iodo, then $R^5$ is not tetrahydrofuranyl or tetrahydropyranyl;

(e) when $R^3$ is methoxy, methylthio, or methylsulfonyl, $R^4$ is hydrogen, and $R^5$ is tetrahydrofuranyl or tetrahydropyranyl, then A is not —NH($C_1$–$C_2$alkyl), morpholinyl, hydrazino, or —$NHC_2H_4C_6H_5$, the phenyl of which may be substituted by one methyl or two methoxy groups;

(f) when $R^3$ is hydrogen, $C_1$–$C_6$ alkyl, chloro, bromo, —SH, or —S—($C_1$–$C_4$ alkyl), $R^4$ is hydrogen and $R^5$ is $C_3$–$C_8$ cycloalkyl, then A is not hydrazino, —NH($C_1$–$C_2$ alkyl) or —N($C_1$–$C_6$ alkyl) ($C_1$–$C_{12}$ alkyl);

(g) when $R^3$ and $R^4$ are hydrogen and A is —NH$(CH_2)_m$COOH wherein m is 1–12, then $R^5$ is not phenyl substituted by one fluoro, chloro, bromo or iodo group;

(h) when $R^3$ is hydrogen, hydroxy, methylthio, chloro or —NHbenzyl, $R^4$ is hydrogen, and $R^5$ is chlorophenyl or bromophenyl, then A is not —NH($C_1$–$C_{12}$ alkyl), —NHallyl, or —N($C_1$–$C_6$ alkyl) ($C_1$–$C_{12}$ alkyl), wherein said $C_1$–$C_{12}$ alkyl may be substituted by —$NC_2H_5$, or —NH benzyl which may be substituted by one or two bromo, chloro, fluoro, —$NC_2H_5$ phenyl or morpholinopropyl groups;

(i) when $R^3$ and $R^4$ are hydrogen and $R^5$ is nitrophenyl, then A is not —$NHR^2$ wherein $R^2$ is phenyl, benzyl or $C_1$–$C_{12}$ alkyl which may be substituted by one or two hydroxy groups;

(j) when $R^3$ is chloro or —O($C_1$–$C_6$ alkyl), $R^4$ is hydrogen, and A is —$NR^1R^2$ wherein $R^1$ and $R^2$ are independently hydrogen or $C_1$–$C_6$ alkyl, then $R^5$ is not chlorophenyl; and (k) when $R^3$ is hydrogen, A is benzyl or phenethyl, and $R^4$ is fluoro, chloro, bromo or iodo, then $R^5$ is not 5'-deoxy-ribofuranosyl or 5'-amino-5'-deoxy-ribofuranosyl; or a pharmaceutically acceptable salt thereof, that is effecting in treating or preventing such disorder, wherein said compound does not substantially inhibit adenosine kinase.

2. A method of treating or preventing a disorder selected from head trauma, spinal cord trauma, muscular spasms, urinary incontinence, multiinfarct dementia, in a mammal in need thereof, comprising administering to such mammal a CRF receptor antagonizing amount of a compound of the formula

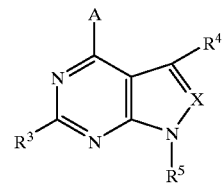

wherein
X is N or —$CR^6$,
A is —$NR^1R^2$, —$CR^1R^2R^{11}$, —$C(=CR^2R^{12})R^1$, —$NHCR^1R^2R^{11}$, —$OCR^1R^2R^{11}$, —$SCR^1R^2R^{11}$, —$NHNR^1R^2$, —$CR^2R^{11}NHR^1$, —$CR^2R^{11}OR^1$, —$CR^2R^{11}SR^1$, or —$C(O)R^2$;

$R^1$ is hydrogen, or $C_1$–$C_6$ alkyl which may optionally be substituted with from one to two substituents independently selected from the group consisting of hydroxy, fluoro, chloro, bromo, iodo, $C_1$–$C_8$ alkoxy, —O—($C_1$–$C_6$ alkyl), —O—NH($C_1$–$C_4$ alkyl), —O—N ($C_1$–$C_4$ alkyl)($C_1$–$C_2$ alkyl), amino, —NH($C_1$–$C_4$ alkyl), —N($C_1$–$C_2$ alkyl)($C_1$–$C_4$ alkyl), —S($C_1$–$C_6$ alkyl), —N($C_1$–$C_4$ alkyl)($C_1$–$C_4$ alkyl), —NH($C_1$–$C_4$ alkyl), —COOH, —O($C_1$–$C_4$ alkyl), —NH($C_1$–$C_4$ alkyl), —N($C_1$–$C_4$ alkyl)($C_1$–$C_2$ alkyl), —SH, —CN, —$NO_2$, —SO($C_1$–$C_4$ alkyl), —$SO_2$($C_1$–$C_4$ alkyl), —$SO_2$NH($C_1$–$C_4$ alkyl), —$SO_2$($C_1$–$C_4$ alkyl)($C_1$–$C_2$ alkyl), and wherein each of the foregoing $C_1$–$C_6$ alkyl moieties in the definition of $R^1$ may contain one or two double or triple bonds;

$R^2$ is $C_1$–$C_{12}$ alkyl, aryl or —($C_1$–$C_{10}$ alkylene)aryl wherein said aryl is phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzisothiazolyl, thiazolyl, isoxazolyl, benzisoxazolyl, benzimidazolyl, triazolyl, pyrazolyl, pyrrolyl, indolyl, pyrrolopyridyl, oxazolyl, or benzoxazolyl; 3- to 8-membered cycloalkyl or —($C_1$–$C_6$ alkylene) cycloalkyl, wherein one or two of the carbon atoms of any of said cycloalkyl moieties may optionally be replaced, independently, by O, S or N-Z wherein Z is hydrogen, $C_1$–$C_4$ alkyl or $C_1$–$C_4$ alkanoyl, and wherein $R^2$ may optionally be substituted with from one to three substituents independently selected from chloro, fluoro and $C_1$–$C_4$ alkyl, or by one substituent selected from hydroxy, bromo, iodo, $C_1$–$C_6$ alkoxy, —O—($C_1$–$C_6$ alkyl), —O—N($C_1$–$C_4$ alkyl)($C_1$–$C_2$ alkyl), —S($C_1$–$C_6$ alkyl), —$NH_2$, —NH($C_1$–$C_2$ alkyl), —N($C_1$–$C_2$ alkyl) ($C_1$–$C_4$ alkyl), —N($C_1$–$C_4$ alkyl)-($C_1$–$C_4$ alkyl), —NH($C_1$–$C_4$ alkyl), —COOH, —O($C_1$–$C_4$ alkyl), —NH($C_1$–$C_4$ alkyl), —N($C_1$–$C_4$ alkyl)($C_1$–$C_2$ alkyl), —SH, —CN, —$NO_2$, —SO ($C_1$–$C_4$ alkyl), —$SO_2$($C_1$–$C_4$ alkyl), —$SO_2$NH($C_1$–$C_4$ alkyl), and —$SO_2$N($C_1$–$C_4$ alkyl)($C_1$–$C_2$ alkyl), and wherein each of the foregoing $C_1$–$C_{12}$ alkyl and $C_1$–$C_{10}$ alkylene moieties in the definition may optionally contain one to three double or triple bonds; or $R^1$ and $R^2$, taken together with the atom to which they are attached, may form a saturated 3- to 8-membered ring which, if it is a 5- to 8-membered ring, may optionally contain one to two double bonds, and wherein one or two of the carbon atoms of said 5- to 8- membered ring may optionally be replaced, independently, by O, S or N-Z wherein Z is hydrogen, $C_1$–$C_4$ alkyl, $C_1$–$C_4$ alkanoyl or benzyl;

$R^3$ is hydrogen, $C_1$–$C_6$ alkyl, fluoro, chloro, bromo, iodo, hydroxy, amino, —O($C_1$–$C_6$ alkyl), —NH($C_1$–$C_6$ alkyl), —N($C_1$–$C_4$ alkyl)($C_1$–$C_2$ alkyl), —SH, —S($C_1$–$C_4$ alkyl), —SO($C_1$–$C_4$ alkyl), or —SO$_2$ ($C_1$–$C_4$ alkyl), wherein each of the foregoing $C_1$–$C_4$ alkyl and $C_1$–$C_6$ alkyl moieties in the definition of $R^3$ may contain one double or triple bond and may optionally be substituted with from 1 to 3 substituents independently selected from the group consisting of hydroxy, $C_1$–$C_3$ alkoxy, fluoro, chloro and $C_1$–$C_3$ thioalkyl;

$R^4$ is hydrogen, $C_1$–$C_6$ alkyl, fluoro, chloro, bromo, iodo, $C_1$–$C_6$ alkoxy, formyl, —NH($C_1$–$C_6$ alkyl), —N($C_1$–$C_6$ alkyl)($C_1$–$C_2$ alkyl), —SO$_n$($C_1$–$C_6$ alkyl), wherein n is 0, 1 or 2, cyano, hydroxy, carboxy, or amido, wherein each of the foregoing $C_1$–$C_6$ alkyl moieties in the definition of $R^3$ may optionally be substituted with one substituent selected from hydroxy, trifluoromethyl, amino, carboxy, amido, —NH($C_1$–$C_4$ alkyl), —NH($C_1$–$C_4$ alkyl), —N($C_1$–$C_4$ alkyl)($C_1$–$C_2$ alkyl), —O($C_1$–$C_4$ alkyl), $C_1$–$C_3$ alkoxy, $C_1$–$C_3$ thioalkyl, fluoro, bromo, chloro, iodo, cyano and nitro;

$R^5$ is phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzoisothiazolyl, thiazolyl, isoxazolyl, benzisoxazolyl, benzimidazolyl, triazolyl, pyrazolyl, pyrrolyl, indolyl, pyrrolopyridyl, benzoxazolyl, oxazolyl, pyrrolidinyl, thiazolindinyl, morpholinyl, piperidinyl, piperazinyl, tetrazolyl, or a 3- or 8-membered cycloalkyl or 9- or 12-membered bicycloalkyl ring, wherein one or two of the carbon atoms in said ring may optionally be replaced, independently, by O, S or N-Z wherein Z is hydrogen, $C_1$–$C_4$ alkyl, $C_1$–$C_4$ alkanoyl, phenyl or benzyl, and wherein each of the above $R^5$ groups may optionally be substituted with one or more substituents, preferably with two or three substituents, independently selected from fluoro, chloro, bromo, formyl, $C_1$–$C_6$ alkyl, $C_1$–$C_6$ alkoxy and trifluoromethyl, or with one substituent selected from hydroxy, iodo, cyano, nitro, amino, —NH($C_1$–$C_4$ alkyl), —N($C_1$–$C_4$ alkyl)($C_1$–$C_2$ alkyl), —COO($C_1$–$C_4$ alkyl), —CO($C_1$–$C_4$ alkyl), —SO$_2$NH($C_1$–$C_4$ alkyl), —SO$_2$N($C_1$–$C_4$ alkyl)($C_1$–$C_2$ alkyl), —SO$_2$NH$_2$, —NHSO$_2$($C_1$–$C_4$ alkyl), —S($C_1$–$C_6$ alkyl), —SO$_2$ ($C_1$–$C_6$ alkyl), and wherein each of the foregoing $C_1$–$C_4$ alkyl and $C_1$–$C_6$ alkyl moieties in the definition of $R^5$ may optionally be substituted with from one to two substituents independently selected from fluoro, chloro, hydroxy, $C_1$–$C_4$ alkoxy, amino, methylamino, dimethylamino and acetyl, and wherein each of the foregoing $C_1$–$C_4$ alkyl and $C_1$–$C_6$ alkyl moieties in the definition of $R^5$ may optionally contain one double or triple bond; with the proviso that $R^5$ is not unsubstituted phenyl;

$R^6$ is hydrogen, $C_1$–$C_6$ alkyl, fluoro, chloro, bromo, iodo, $C_1$–$C_6$ alkoxy, formyl, amino, —NH($C_1$–$C_6$ alkyl), N($C_1$–$C_6$ alkyl)($C_1$–$C_2$ alkyl), —SO$_n$($C_1$–$C_6$ alkyl), wherein n is 0, 1 or 2, cyano, carboxy, or amido, and wherein each of the foregoing ($C_1$–$C_6$)alkyl moieties in the definition of $R^6$ may be optionally substituted with one substituent selected from hydroxy, trifluoromethyl, amino, carboxy, amido, —NH($C_1$–$C_4$ alkyl), —NH ($C_1$–$C_4$ alkyl), —N($C_1$–$C_4$ alkyl)($C_1$–$C_2$ alkyl), —O($C_1$–$C_4$ alkyl), $C_1$–$C_3$ alkoxy, $C_1$–$C_3$ thioalkyl, fluoro, bromo, chloro, iodo, cyano and nitro;

$R^{11}$ is hydrogen, hydroxy, fluoro, chloro, —COO($C_1$–$C_2$ alkyl), cyano, or —CO($C_1$–$C_2$ alkyl); and $R^{12}$ is hydrogen or $C_1$–$C_4$ alkyl;

with the proviso that:

(1) when X is —CR$^6$, A is not straight chain alkyl;

(2) when X is —CR$^6$ and $R^5$ is unsubstituted cycloalkyl and $R^3$ and $R^4$ are both hydrogen and $R^6$ is hydrogen or methyl, then A is not NHR$^2$ wherein $R^2$ is benzyl or thienylmethyl, and (3) when X is —CR$^6$ and $R^5$ is p-bromophenyl and $R^3$, $R^4$ and $R^6$ are methyl, then A is not methylamino or hydroxyethylamino;

and when X is nitrogen, with the further proviso that:

(a) A is not straight chain $C_1$–$C_{12}$ alkyl;

(b) $R^5$ is not a sugar group;

(c) when $R^3$ and $R^4$ are hydrogen and $R^5$ is chlorophenyl, then A is not —NH—CH(CH$_3$)—(CH$_2$)$_3$—(C$_2$H$_5$)$_2$;

(d) when $R^3$ and $R^4$ are hydrogen and A is —NR$^1$R$^2$ wherein $R^1$ is $C_3$–$C_7$ cycloalkyl, and $R^2$ is $C_2$–$C_6$ alkenyl, phenyl-($C_1$–$C_6$ alkylene) or hetero-($C_1$–$C_6$ alkylene) wherein the hetero radical is furyl, thienyl or pyridinyl, and wherein said phenyl may be substituted with one or more substituents independently selected from fluoro, chloro, bromo and iodo, then $R^5$ is not tetrahydrofuranyl or tetrahydropyranyl;

(e) when $R^3$ is methoxy, methylthio, or methylsulfonyl, $R^4$ is hydrogen, and $R^5$ is tetrahydrofuranyl or tetrahydropyranyl, then A is not —NH($C_1$–$C_2$alkyl), morpholinyl, hydrazino, or —NHC$_2$H$_4$C$_6$H$_5$, the phenyl of which may be substituted by one methyl or two methoxy groups;

(f) when $R^3$ is hydrogen, $C_1$–$C_6$ alkyl, chloro, bromo, —SH, or —S—($C_1$–$C_4$ alkyl), $R^4$ is hydrogen and $R^5$ is $C_3$–$C_8$ cycloalkyl, then A is not hydrazino, —NH ($C_1$–$C_2$ alkyl) or —N($C_1$–$C_6$ alkyl) ($C_1$–$C_{12}$ alkyl);

(g) when $R^3$ and $R^4$ are hydrogen and A is —NH(CH$_2$)$_m$COOH wherein m is 1–12, then $R^5$ is not phenyl substituted by one fluoro, chloro, bromo or iodo group;

(h) when $R^3$ is hydrogen, hydroxy, methylthio, chloro or —NHbenzyl, $R^4$ is hydrogen, and $R^5$ is chlorophenyl or bromophenyl, then A is not —NH($C_1$–$C_{12}$ alkyl), —NHallyl, or —N($C_1$–$C_6$ alkyl) ($C_1$–$C_{12}$ alkyl), wherein said $C_1$–$C_{12}$ alkyl may be substituted by —NC$_2$H$_5$, or —NH benzyl which may be substituted by one or two bromo, chloro, fluoro, —NC$_2$H$_5$ phenyl or morpholinopropyl groups;

(i) when $R^3$ and $R^4$ are hydrogen and $R^5$ is nitrophenyl, then A is not —NHR$^2$ wherein $R^2$ is phenyl, benzyl or $C_1$–$C_{12}$ alkyl which may be substituted by two hydroxy groups;

(j) when $R^3$ is chloro or —O($C_1$–$C_6$ alkyl), $R^4$ is hydrogen, and A is —NR$^1$R$^2$ wherein $R^1$ and $R^2$ are independently hydrogen or $C_1$–$C_6$ alkyl, then $R^5$ is not chlorophenyl; and (k) when $R^3$ is hydrogen, A is benzyl or phenethyl, and $R^4$ is fluoro, chloro, bromo or iodo, then $R^5$ is not 5'-deoxy-ribofuranosyl or 5'-amino-5'-deoxy-ribofuranosyl; or a pharmaceutically acceptable salt thereof, wherein said compound does not substantially inhibit adenosine kinase.

3. A method according to claim 1, wherein the compound of formula I or the pharmaceutically acceptable salt of such compound that is employed is a compound wherein X is nitrogen and:

(a) $R^1$ is $C_1$–$C_4$ alkyl, —($C_2$–$C_4$ alkylene)O($C_1$–$C_4$ alkyl), or $C_2$–$C_4$ hydroxyalkyl;

(b) $R^2$ is $C_1$–$C_5$ alkyl, benzyl, phenylethyl, or benzyl substituted with one or two substituents independently selected from chloro, fluoro, methyl, ethyl, methoxy, ethoxy and t-butyl, or with one trifluoromethyl group; (2-thienyl)methyl; (2-thienyl)ethyl; (2-furanyl)methyl; 2-(4-chlorothienyl)methyl; (2-benzofuranyl)methyl; (2-benzothienyl)methyl; (2-thiazolyl) methyl; or (2-benzothiazolyl)methyl;

(c) $R^3$ is hydrogen, methyl, ethyl, methoxy, fluoro or chloro;

(d) $R^4$ is hydrogen, methyl, ethyl, or n-propyl; and (e) $R^5$ is phenyl substituted by two or three substituents.

4. A method according to claim 1, wherein the compound of formula I or the pharmaceutically acceptable salt of such compound that is employed is a compound wherein X is —$CR^6$ and:

(a) $R^1$ is $C_1$–$C_4$ alkyl, —($C_2$–$C_4$ alkylene)O($C_1$–$C_4$ alkyl), or $C_2$–$C_4$ hydroxyalkyl;

(b) $R^2$ is $C_1$–$C_5$ alkyl, benzyl, phenylethyl, or benzyl substituted with one or two substituents independently selected from chloro, fluoro, methyl, ethyl, methoxy, ethoxy and t-butyl, or with one trifluoromethyl group; (2-thienyl)methyl; (2-thienyl)ethyl; (2-furanyl)methyl; 2-(4-chlorothienyl)methyl; (2-benzofuranyl)methyl; (2-benzothienyl)methyl; (2-thiazolyl) methyl; or (2-benzothiazolyl)methyl;

(c) $R^3$ is hydrogen, methyl, ethyl, methoxy, fluoro or chloro;

(d) $R^4$ is hydrogen, methyl, ethyl, or n-propyl;

(e) $R^5$ is phenyl substituted by two or three substituents; and (f) $R^6$ is hydrogen, methyl, ethyl or chloro; with the proviso that $R^2$ and $R^6$ are not both hydrogen.

5. A method according to claim 1, wherein the compound of formula I or the pharmaceutically acceptable salt of such compound that is employed is a compound wherein X is nitrogen and:

(a) A is —$NR^1R^2$, —$NHCHR^1R^2$, or —$OCHR^1R^2$, wherein $R^1$ is $C_1$–$C_6$ alkyl, which may optionally be substituted by one hydroxy, fluoro or $C_1$–$C_2$ alkoxy group, and which may optionally contain one double or triple bond, and $R^2$ is benzyl or $C_1$–$C_6$ alkyl which may optionally contain one double or triple bond, wherein said $C_1$–$C_6$ alkyl or the phenyl moiety or said benzyl may optionally be substituted with one fluoro, $C_1$–$C_6$ alkyl, or $C_1$–$C_6$ alkoxy group; or (b) A is —$CR^1R^2R^{11}$ wherein $R^1$ is $C_1$–$C_6$ alkyl which may optionally be substituted with one $C_1$–$C_6$ alkoxy or hydroxy group, $R^2$ is benzyl or $C_1$–$C_6$ alkyl wherein said $C_1$–$C_6$ alkyl or the phenyl in said benzyl may optionally be substituted by one $C_1$–$C_6$ alkyl, $C_1$–$C_6$ alkoxy, fluoro, chloro or bromo group, and $R^{11}$ is hydrogen or fluoro.

6. A method according to claim 1, wherein the compound of formula I, or the pharmaceutically acceptable salt of such compound that is employed is a compound wherein X is nitrogen and $R^2$ is —($C_1$–$C_4$ alkylene)aryl wherein said aryl is phenyl, thienyl, benzofuranyl, furanyl, benzothienyl, thiazolyl, pyridyl or benzothiazolyl.

7. A method according to claim 1, wherein the compound of formula I, or the pharmaceutically acceptable salt of such compound that is employed is a compound wherein X is nitrogen and $R^2$ is benzyl optionally substituted on the phenyl moiety with one ethyl, t-butyl, methoxy, trifluoromethyl, nitro, fluoro, chloro, or methyl group.

8. A method according to claim 1, wherein the compound of formula I, or the pharmaceutically acceptable salt of such compound that is employed is a compound wherein X is nitrogen and $R^2$ is attached through a methylene or ethylene bridge to quinolyl, pyrrolyl, pyrrolidinyl, pyridyl, tetrahydropyranyl, cyclopropyl, piperidinyl, or benzyl-piperidinyl.

9. A method according to claim 1, wherein the compound of formula I, or the pharmaceutically acceptable salt of such compound that is employed is a compound wherein X is nitrogen or —$CR^6$ and $R^1$ and $R^2$ are, independently, $C_1$–$C_6$ alkyl which may optionally be substituted with one hydroxy, methoxy, ethoxy, chloro, fluoro, —$OC(O)CH_3$, —$OC(O)NHCH_3$, or —$C(O)NH_2$ group.

10. A method according to claim 1, wherein the compound of formula I, or the pharmaceutically acceptable salt of such compound that is employed is a compound wherein X is nitrogen or —$CR^6$ and $R^2$ is $C_1$–$C_6$ alkyl substituted with one substituent selected from methoxy and ethoxy.

11. A method according to claim 1, wherein the compound of formula I, or the pharmaceutically acceptable salt of such compound that is employed is a compound wherein X is nitrogen and A is —$NR^1R^2$ or —$CHR^1R^2$ in which $R^1$ and $R^2$, together with the N or CH to which they are attached, form a 5- or 6-membered ring in which one of the ring carbons may optionally be replaced by an oxygen or sulfur atom.

12. A method according to claim 1, wherein the compound of formula I, or the pharmaceutically acceptable salt of such compound that is employed is a compound wherein X is nitrogen or —$CR^6$ and A is —$NHCHR^1R^2$ or —$OCHR^1R^2$ in which $CHR^1R^2$ is a 5- or 6-membered ring in which one of the ring carbons may optionally be replaced by an oxygen or sulfur atom.

13. A method according to claim 1, wherein the compound of formula I or the pharmaceutically acceptable salt of such compound that is employed is a compound wherein X is nitrogen and:

(a) A is —$NR^1R^2$, —$NHCHR^1R^2$, or —$OCHR^1R^2$, wherein $R^1$ is $C_1$–$C_6$ alkyl, which may optionally be substituted with one hydroxy, fluoro or $C_1$–$C_2$ alkoxy group and may optionally contain one double or triple bond;

(b) $R^2$ is benzyl or $C_1$–$C_6$ alkyl which may optionally contain one double or triple bond, wherein said $C_1$–$C_6$ alkyl or the phenyl in said benzyl may optionally be substituted with fluoro, $C_1$–$C_6$ alkyl, or $C_1$–$C_6$ alkoxy;

(c) $R^3$ is methyl, ethyl, fluoro, chloro or methoxy;

(c) $R^4$ and $R^6$ are independently selected from hydrogen, methyl and ethyl; and (d) $R^5$ is phenyl substituted by two or three substituents, said substituents being independently selected from fluoro, chloro, bromo, iodo, $C_1$–$C_4$ alkoxy, trifluoromethyl, $C_1$–$C_6$ alkyl which may optionally be substituted with one hydroxy, $C_1$–$C_4$ alkoxy or fluoro group and which may optionally contain one double or triple bond, —($C_1$–$C_4$ alkylene)O($C_1$–$C_2$ alkyl), $C_1$–$C_3$ hydroxyalkyl, hydroxy, formyl, —$COO(C_1$–$C_2$ alkyl) and —$C(O)(C_1$–$C_4$ alkyl).

14. A method according to claim 1, wherein the compound of formula I or the pharmaceutically acceptable salt of such compound that is employed is a compound wherein X is $CR^6$ and:

(a) A is —$NR^1R^2$, —$NHCHR^1R^2$, or —$OCHR^1R^2$, wherein $R^1$ is $C_1$–$C_6$ alkyl, which may optionally be substituted with one hydroxy, fluoro or $C_1$–$C_2$ alkoxy group and may optionally contain one double or triple bond;

(b) $R^2$ is benzyl or $C_1$–$C_6$ alkyl which may optionally contain one double or triple bond, wherein said $C_1$–$C_6$ alkyl or the phenyl in said benzyl may optionally be substituted with fluoro, $C_1$–$C_6$ alkyl, or $C_1$–$C_6$ alkoxy;

(c) $R^3$ is methyl, ethyl, fluoro, chloro or methoxy;

(c) $R^4$ and $R^6$ are independently selected from hydrogen, methyl and ethyl; and (d) $R^5$ is phenyl substituted by two or three substituents, said substituents being independently selected from fluoro, chloro, bromo, iodo, $C_1$–$C_4$ alkoxy, trifluoromethyl, $C_1$–$C_6$ alkyl which may optionally be substituted with one hydroxy, $C_1$–$C_4$ alkoxy or fluoro group and which may optionally contain one double or triple bond, —($C_1$–$C_4$ alkylene)O($C_1$–$C_2$ alkyl), $C_1$–$C_3$ hydroxyalkyl, hydroxy, formyl, —COO($C_1$–$C_2$ alkyl) and —C(O)($C_1$–$C_4$ alkyl).

15. A method according to claim 1, wherein the compound of formula I, or the pharmaceutically acceptable salt of such compound that is employed is a compound selected from the following:

3-{(4-methyl-benzyl)-[3,6-dimethyl-1-(2,4,6-trimethylphenyl)-1H-pyrazolo[3,4-d]pyrimidin-4yl]-amino}-propan-1-ol;

diethyl-[6-methyl-3-methylsulfanyl-1-(2,4,6-trichlorophenyl)-1H-pyrazolo[3,4-d]pyrimidin-4yl]-amine;

2-{butyl-[6-methyl-3-methylsulfanyl-1-(2,4,6-trichlorophenyl)-1H-pyrazolo[3,4-d]pyrimidin-4yl]-amino}-ethanol;

dibutyl-[6-methyl-3-methylsulfanyl-1-(2,4,6-trichlorophenyl)-1H-pyrazolo[3,4-d]pyrimidin-4yl}-amine;

butyl-ethyl-[6-methyl-3-methylsulfanyl-1-(2,4,6-trichlorophenyl)-1H-pyrazolo[3,4-d]pyrimidin-4yl]-amine;

butyl-ethyl-[6-methyl-3-methylsulfonyl-1-(2,4,6-trichlorophenyl)-1H-pyrazolo[3,4-d]pyrimidin-4yl]-amine;

butyl-cyclopropylmethyl-[6-methyl-3-methylsulfanyl-1-(2,4,6-trichlorophenyl)-1H-pyrazolo[3,4-d]pyrimidin-4yl]-amine;

di-1-propyl-[6-methyl-3-methylsulfanyl-1-(2,4,6-trichlorophenyl)-1H-pyrazolo[3,4-d]pyrimidin-4yl]-amine;

diallyl-[6-methyl-3-methylsulfanyl-1-(2,4,6-trichlorophenyl)-1H-pyrazolo[3,4-d]pyrimidin-4yl]-amine;

butyl-ethyl-[6-chloro-3-methylsulfanyl-1-(2,4,6-trichlorophenyl)-1H-pyrazolo[3,4-d]pyrimidin-4yl]-amine;

butyl-ethyl-[6-methoxy-3-methylsulfanyl-1-(2,4,6-trichlorophenyl)-1H-pyrazolo[3,4-d]pyrimidin-4yl]-amine;

propyl-ethyl-[3,6-dimethyl-1-(2,4,6-trimethylphenyl)-1H-pyrazolo[3,4-d]pyrimidin-4-yl]-amine;

4-(1-ethyl-propyl)-6-methyl-3-methylsulfanyl-1-(2,4,6-trimethylphenyl)-1H-pyrazolo[3,4-d]pyrimidine;

2-[3,6-dimethyl-1-(2,4,6-trimethylphenyl)-1H-pyrazolo[3,4-d]pyrimidin-4-ylamine]-butan-1ol;

[3,6-dimethyl-1-(2,4,6-trimethylphenyl)-1H-pyrazolo-[3,4-d]pyrimidin-4-yl]-(1-methylpropyl)amine;

4-(1-methoxymethylpropoxy)-3,6-dimethyl-1-(2,4,6-trimethylphenyl)-1H-pyrazolo[3,4-d]pyrimidine;

n-butyl-ethyl-[2,5-dimethyl-7-(2,4,6-trimethylphenyl)-7H-pyrrolo[2,3-d]pyrimidin-4-yl]amine;

di-n-propyl-[2,5-dimethyl-7-(2,4,6-trimethylphenyl)-7H-pyrrolo[2,3-d]pyrimidin-4-yl]amine;

ethyl-n-propyl-[2,5-dimethyl-7-(2,4,6-trimethylphenyl)-7H-pyrrolo[2,3-d]pyrimidin-4-yl]amine;

diethyl-2,5-dimethyl-7-(2,4,6-trimethylphenyl)-7H-pyrrolo[2,3-d]pyrimidin-4-yl]amine;

n-butyl-ethyl-[2,5,6-trimethyl-7-(2,4,6-trimethylphenyl)-7H-pyrrolo[2,3-d]pyrimidin-4-yl]amine;

2{N-n-butyl-N-[2,5-dimethyl-7-(2,4,6-trimethylphenyl)-7H-pyrrolo[2,3-d]pyrimidin-4-yl]amino}-ethanol;

4-(1-ethyl-propyl)-2,5,6-trimethyl-7-(2,4,6-trimethylphenyl)-7H-pyrrolo[2,3-d]pyrimidine;

n-butyl-ethyl-[2,5-dimethyl-7-(2,4-dimethylphenyl)-7H-pyrrolo[2,3-d]pyrimidin-4-yl]amine;

2,5-dimethyl-7-(2,4,6-trimethylphenyl)-7H-pyrrolo[2,3-d]pyrimidyl-4-yl]-(1-ethylpropyl)amine;

2-[7-(4-bromo-2,6-dimethylphenyl)-2,5-dimethyl-7H-pyrrolo[2,3-d]pyrimidin-4-ylamino]-butan-1-ol;

2-(S)-[7-(4-bromo-2,6-dimethylphenyl)-2,5-dimethyl-7H-pyrrolo[2,3-d]pyrimidin-4-ylamino]-butan-1-ol;

4-(1-ethyl-propoxy)-2,5,6-trimethyl-7-(2,4,6-trimethylphenyl)-7H-pyrrolo[2,3-d]pyrimidine;

4-(1-methoxymethyl-propoxy)-2,5,6-trimethyl-7-(2,4,6-trimethylphenyl)-7H-pyrrolo[2,3-d]pyrimidine;

4-(1-ethyl-butyl)-2,5,6-trimethyl-7-(2,4,6-trimethylphenyl)-7H-pyrrolo[2,3-d]pyrimidine;

[7-(4-bromo-2,6-dimethyl-phenyl)-2,5-dimethyl-7H-pyrrolo[2,3-d]pyrimidin-4yl]-(1-methoxymethyl-propyl)-amine;

2-[7-(2-bromo-4,6-dimethyl-phenyl)-2,5-dimethyl-7H-pyrrolo[2,3-d]pyrimidin-4ylamino]-butan-1-ol;

2-[7-(4-ethyl-2,6-dimethyl-phenyl)-2,5-dimethyl-7H-pyrrolo[2,3-d]pyrimidin-4ylamino]-butan-1-ol;

2-[7-(2-ethyl-4,6-dimethylphenyl)-2,5-dimethyl-7H-pyrrolo[2,3-d]pyrimidin-4ylamino]-butan-1-ol; and 2-[7-(2-fluoromethyl-4,6-dimethylphenyl)-2,5-dimethyl-7H-pyrrolo[2,3-d]pyrimidin-4ylamino]-butan-1-ol.

16. A method according to claim 2, wherein the compound of formula I or the pharmaceutically acceptable salt of such compound that is employed is a compound wherein X is nitrogen and:

(a) $R^1$ is $C_1$–$C_4$ alkyl, —($C_2$–$C_4$ alkylene)O($C_1$–$C_4$ alkyl), or $C_2$–$C_4$ hydroxyalkyl;

(b) $R^2$ is $C_1$–$C_5$ alkyl, benzyl, phenylethyl, or benzyl substituted with one or two substituents independently selected from chloro, fluoro, methyl, ethyl, methoxy, ethoxy and t-butyl, or with one trifluoromethyl group; (2-thienyl)methyl; (2-thienyl)ethyl; (2-furanyl)methyl; 2-(4-chlorothienyl)methyl; (2-benzofuranyl)methyl; (2-benzothienyl)methyl; (2-thiazolyl) methyl; or (2-benzothiazolyl)methyl;

(c) $R^3$ is hydrogen, methyl, ethyl, methoxy, fluoro or chloro;

(d) $R^4$ is hydrogen, methyl, ethyl, or n-propyl; and (e) $R^5$ is phenyl substituted by two or three substituents.

17. A method according to claim 2, wherein the compound of formula I or the pharmaceutically acceptable salt of such compound that is employed is a compound wherein X is —$CR^6$ and:

(a) $R^1$ is $C_1$–$C_4$ alkyl, —($C_2$–$C_4$ alkylene)O($C_1$–$C_4$ alkyl), or $C_2$–$C_4$ hydroxyalkyl;

(b) $R^2$ is $C_1$–$C_5$ alkyl, benzyl, phenylethyl, or benzyl substituted with one or two substituents independently selected from chloro, fluoro, methyl, ethyl, methoxy, ethoxy and t-butyl, or with one trifluoromethyl group; (2-thienyl)methyl; (2-thienyl)ethyl; (2-furanyl)methyl; 2-(4-chlorothienyl)methyl; (2-benzofuranyl)methyl; (2-benzothienyl)methyl; (2-thiazolyl) methyl; or (2-benzothiazolyl)methyl;

(c) $R^3$ is hydrogen, methyl, ethyl, methoxy, fluoro or chloro;

(d) $R^4$ is hydrogen, methyl, ethyl, or n-propyl;

(e) $R^5$ is phenyl substituted by two or three substituents; and (f) $R^6$ is hydrogen, methyl, ethyl or chloro; with the proviso that $R^4$ and $R^6$ are not both hydrogen.

18. A method according to claim 2, wherein the compound of formula I or the pharmaceutically acceptable salt of such compound that is employed is a compound wherein X is nitrogen and either:

(a) A is —$NR^1R^2$, —$NHCHR^1R^2$, or —$OCHR^1R^2$, wherein $R^1$ is $C_1$–$C_6$ alkyl, which may optionally be substituted with one hydroxy, fluoro or $C_1$–$C_2$ alkoxy group, and which may optionally contain one double or triple bond, and $R^2$ is benzyl or $C_1$–$C_6$ alkyl which may optionally contain one double or triple bond, wherein said $C_1$–$C_6$ alkyl or the phenyl moiety of said benzyl may optionally be substituted with one fluoro, $C_1$–$C_6$ alkyl, or $C_1$–$C_6$ alkoxy group; or (b) A is $CR^1R^2R^{11}$ wherein $R^1$ is $C_1$–$C_6$ alkyl which may optionally be substituted with one $C_1$–$C_6$ alkoxy or hydroxy group, $R^2$ is benzyl or $C_1$–$C_6$ alkyl wherein $C_1$–$C_6$ alkyl or the phenyl in said benzyl may optionally be substituted by one $C_1$–$C_6$ alkyl, $C_1$–$C_6$ alkoxy, fluoro, chloro or bromo group, and $R^{11}$ is hydrogen or fluoro.

19. A method according to claim 2, wherein the compound of formula I, or the pharmaceutically acceptable salt of such compound that is employed is a compound wherein X is nitrogen and $R^2$ is —($C_1$–$C_4$ alkylene)aryl wherein said aryl is phenyl, thienyl, benzofuranyl, furanyl, benzothienyl, thiazolyl, pyridyl or benzothiazolyl.

20. A method according to claim 2, wherein the compound of formula I, or the pharmaceutically acceptable salt of such compound that is employed is a compound wherein X is nitrogen and $R^2$ is benzyl optionally substituted on the phenyl moiety with one ethyl, t-butyl, methoxy, trifluoromethyl, nitro, fluoro chloro or methyl group.

21. A method according to claim 2, wherein the compound of formula I, or the pharmaceutically acceptable salt of such compound that is employed is a compound wherein X is nitrogen and $R^2$ is attached through a methylene or ethylene bridge to quinolyl, pyrrolyl, pyrrolidinyl, pyridyl, tetrahydropyranyl, cyclopropyl, piperidinyl, or benzylpiperidinyl.

22. A method according to claim 2, wherein the compound of formula I, or the pharmaceutically acceptable salt of such compound that is employed is a compound wherein X is nitrogen or —$CR^6$ and $R^1$ and $R^2$ are, independently, $C_1$–$C_6$ alkyl which may optionally be substituted with one hydroxy, methoxy, ethoxy, chloro, fluoro, —$OC(O)CH_3$, —$OC(O)NHCH_3$, or —$C(O)NH_2$ group.

23. A method according to claim 2, wherein the compound of formula I, or the pharmaceutically acceptable salt of such compound that is employed is a compound wherein X is nitrogen or —$CR^6$ and $R^2$ is $C_1$–$C_6$ alkyl substituted with one substituent selected from methoxy and ethoxy.

24. A method according to claim 2, wherein the compound of formula I, or the pharmaceutically acceptable salt of such compound that is employed is a compound wherein X is nitrogen and A is —$NR^1R^2$ or —$CHR^1R^2$ in which $R^1$ and $R^2$, taken together with the N or CH to which they are attached, form a 5- or 6-membered ring in which one of the ring carbon atoms may optionally be replaced by a sulfur or oxygen atom.

25. A method according to claim 2, wherein the compound of formula I, or the pharmaceutically acceptable salt of such compound that is employed is a compound wherein X is nitrogen and A is —$NHCHR^1R^2$ or —$OCHR^1R^2$ in which $CHR^1R^2$ is a 5- or 6-membered ring in which one of the ring carbon atoms may optionally be replaced by an oxygen or sulfur atom.

26. A method according to claim 2, wherein the compound of formula I or the pharmaceutically acceptable salt of such compound that is employed is a compound wherein X is $CR^6$ and:

(a) A is —$NR^1R^2$, —$NHCHR^1R^2$, or —$OCHR^1R^2$, wherein $R^1$ is $C_1$–$C_6$ alkyl, which may optionally be substituted with one hydroxy, fluoro or $C_1$–$C_2$ alkoxy group and may optionally contain one double or triple bond;

(b) $R^2$ is benzyl or $C_1$–$C_6$ alkyl which may optionally contain one double or triple bond, wherein said $C_1$–$C_6$ alkyl or the phenyl in said benzyl may optionally be substituted with fluoro, $C_1$–$C_6$ alkyl, or $C_1$–$C_6$ alkoxy;

(c) $R^3$ is methyl, ethyl, fluoro, chloro or methoxy;

(c) $R^4$ and $R^6$ are independently selected from hydrogen, methyl and ethyl; and (d) $R^5$ is phenyl substituted by two or three substituents, said substituents being independently selected from fluoro, chloro, bromo, iodo, $C_1$–$C_4$ alkoxy, trifluoromethyl, $C_1$–$C_6$ alkyl which may optionally be substituted with one hydroxy, $C_1$–$C_4$ alkoxy or fluoro group and which may optionally contain one double or triple bond, —($C_1$–$C_4$ alkylene)O($C_1$–$C_2$ alkyl), $C_1$–$C_3$ hydroxyalkyl, hydroxy, formyl, —$COO(C_1$–$C_2$ alkyl), and —$C(O)(C_1$–$C_4$ alkyl).

27. A method according to claim 2, wherein the compound of formula I or the pharmaceutically acceptable salt of such compound that is employed is a compound wherein X is nitrogen and:

(a) A is —$NR^1R^2$, —$NHCHR^1R^2$, or —$OCHR^1R^2$, wherein $R^1$ is $C_1$–$C_6$ alkyl, which may optionally be substituted with one hydroxy, fluoro or $C_1$–$C_2$ alkoxy group and may optionally contain one double or triple bond;

(b) $R^2$ is benzyl or $C_1$–$C_6$ alkyl which may optionally contain one double or triple bond, wherein said $C_1$–$C_6$ alkyl or the phenyl in said benzyl may optionally be substituted with fluoro, $C_1$–$C_6$ alkyl, or $C_1$–$C_6$ alkoxy;

(c) $R^3$ is methyl, ethyl, fluoro, chloro or methoxy;

(c) $R^4$ and $R^6$ are independently selected from hydrogen, methyl and ethyl; and (d) $R^5$ is phenyl substituted by two or three substituents, said substituents being independently selected from fluoro, chloro, bromo, iodo, $C_1$–$C_4$ alkoxy, trifluoromethyl, $C_1$–$C_6$ alkyl which may optionally be substituted with one hydroxy, $C_1$–$C_4$ alkoxy or fluoro group and which may optionally contain one double or triple bond, —($C_1$–$C_4$ alkylene)O($C_1$–$C_2$ alkyl), $C_1$–$C_3$ hydroxyalkyl, hydroxy, formyl, —$COO(C_1$–$C_2$ alkyl) and —$C(O)(C_1$–$C_4$ alkyl).

28. A method according to claim 2, wherein the compound of formula I, or the pharmaceutically acceptable salt of such compound that is employed is a compound selected from the following:

- 3-{(4-methyl-benzyl)-[3,6-dimethyl-1-(2,4,6-trimethylphenyl)-1H-pyrazolo[3,4-d]pyrimidin-4yl]-amino}-propan-1-ol;
- diethyl-[6-methyl-3-methylsulfanyl-1-(2,4,6-trichlorophenyl)-1H-pyrazolo[3,4-d]pyrimidin-4yl]-amine;
- 2-{butyl-[6-methyl-3-methylsulfanyl-1-(2,4,6-trichlorophenyl)-1H-pyrazolo[3,4-d]pyrimidin-4yl]-amino}-ethanol;
- dibutyl-[6-methyl-3-methylsulfanyl-1-(2,4,6-trichlorophenyl)-1H-pyrazolo[3,4-d]pyrimidin-4yl}-amine;
- butyl-ethyl-[6-methyl-3-methylsulfanyl-1-(2,4,6-trichlorophenyl)-1H-pyrazolo[3,4-d]pyrimidin-4yl]-amine;
- butyl-ethyl-[6-methyl-3-methylsulfonyl-1-(2,4,6-trichlorophenyl)-1H-pyrazolo[3,4-d]pyrimidin-4yl]-amine;
- butyl-cyclopropylmethyl-[6-methyl-3-methylsulfanyl-1-(2,4,6-trichlorophenyl)-1H-pyrazolo[3,4-d]pyrimidin-4yl]-amine;
- di-1-propyl-[6-methyl-3-methylsulfanyl-1-(2,4,6-trichlorophenyl)-1H-pyrazolo[3,4-d]pyrimidin-4yl]-amine;
- diallyl-[6-methyl-3-methylsulfanyl-1-(2,4,6-trichlorophenyl)-1H-pyrazolo[3,4-d]pyrimidin-4yl]-amine;
- butyl-ethyl-[6-chloro-3-methylsulfanyl-1-(2,4,6-trichlorophenyl)-1H-pyrazolo[3,4-d]pyrimidin-4yl]-amine;
- butyl-ethyl-[6-methoxy-3-methylsulfanyl-1-(2,4,6-trichlorophenyl)-1H-pyrazolo[3,4-d]pyrimidin-4yl]-amine;
- propyl-ethyl-[3,6-dimethyl-1-(2,4,6-trimethylphenyl)-1H-pyrazolo[3,4-d]pyrimidin-4-yl]-amine;
- 4-(1-ethyl-propyl)-6-methyl-3-methylsulfanyl-1-(2,4,6-trimethylphenyl)-1H-pyrazolo[3,4-d]pyrimidine;
- 2-[3,6-dimethyl-1-(2,4,6-trimethylphenyl)-1H-pyrazolo[3,4-d]pyrimidin-4-ylamine]-butan-1ol;
- [3,6-dimethyl-1-(2,4,6-trimethylphenyl)-1H-pyrazolo-[3,4-d]pyrimidin-4-yl]-(1-methylpropyl)amine;
- 4-(1-methoxymethylpropoxy)-3,6-dimethyl-1-(2,4,6-trimethylphenyl)-1H-pyrazolo[3,4-d]pyrimidine;
- n-butyl-ethyl-[2,5-dimethyl-7-(2,4,6-trimethylphenyl)-7H-pyrrolo[2,3-d]pyrimidin-4-yl]amine;
- di-n-propyl-[2,5-dimethyl-7-(2,4,6-trimethylphenyl)-7H-pyrrolo[2,3-d]pyrimidin-4-yl]amine;
- ethyl-n-propyl-[2,5-dimethyl-7-(2,4,6-trimethylphenyl)-7H-pyrrolo[2,3-d]pyrimidin-4-yl]amine;
- diethyl-2,5-dimethyl-7-(2,4,6-trimethylphenyl)-7H-pyrrolo[2,3-d]pyrimidin-4-yl]amine;
- n-butyl-ethyl-[2,5,6-trimethyl-7-(2,4,6-trimethylphenyl)-7H-pyrrolo[2,3-d]pyrimidin-4-yl]amine;
- 2{N-n-butyl-N-[2,5-dimethyl-7-(2,4,6-trimethylphenyl)-7H-pyrrolo[2,3-d]pyrimidin-4-yl]amino}-ethanol;
- 4-(1-ethyl-propyl)-2,5,6-trimethyl-7-(2,4,6-trimethylphenyl)-7H-pyrrolo[2,3-d]pyrimidine;
- n-butyl-ethyl-[2,5-dimethyl-7-(2,4-dimethylphenyl)-7H-pyrrolo[2,3-d]pyrimidin-4-yl]amine;
- 2,5-dimethyl-7-(2,4,6-trimethylphenyl)-7H-pyrrolo[2,3-d]pyrimidyl-4-yl]-(1-ethylpropyl)amine;
- 2-[7-(4-bromo-2,6-dimethylphenyl)-2,5-dimethyl-7H-pyrrolo[2,3-d]pyrimidin-4-ylamino]-butan-1-ol;
- 2-(S)-[7-(4-bromo-2,6-dimethylphenyl)-2,5-dimethyl-7H-pyrrolo[2,3-d]pyrimidin-4-ylamino]-butan-1-ol;
- 4-(1-ethyl-propoxy)-2,5,6-trimethyl-7-(2,4,6-trimethylphenyl)-7H-pyrrolo[2,3-d]pyrimidine;
- 4-(1-methoxymethyl-propoxy)-2,5,6-trimethyl-7-(2,4,6-trimethylphenyl)-7H-pyrrolo[2,3-d]pyrimidine;
- 4-(1-ethyl-butyl)-2,5,6-trimethyl-7-(2,4,6-trimethylphenyl)-7H-pyrrolo[2,3-d]pyrimidine;
- [7-(4-bromo-2,6-dimethyl-phenyl)-2,5-dimethyl-7H-pyrrolo[2,3-d]pyrimidin-4yl]-(1-methoxymethyl-propyl)-amine;
- 2-[7-(2-bromo-4,6-dimethyl-phenyl)-2,5-dimethyl-7H-pyrrolo[2,3-d]pyrimidin-4ylamino]-butan-1-ol;
- 2-[7-(4-ethyl-2,6-dimethyl-phenyl)-2,5-dimethyl-7H-pyrrolo[2,3-d]pyrimidin-4ylamino]-butan-1-ol;
- 2-[7-(2-ethyl-4,6-dimethylphenyl)-2,5-dimethyl-7H-pyrrolo[2,3-d]pyrimidin-4ylamino]-butan-1-ol; and
- 2-[7-(2-fluoromethyl-4,6-dimethylphenyl)-2,5-dimethyl-7H-pyrrolo[2,3-d]pyrimidin-4ylamino]-butan-1-ol.

* * * * *